United States Patent
Cook et al.

(10) Patent No.: US 9,364,037 B2
(45) Date of Patent: Jun. 14, 2016

(54) LIMITED DURABILITY FASTENING FOR A GARMENT

(71) Applicant: Covidien AG, Neuhausen (CH)

(72) Inventors: Gordon J. Cook, Hampshire (GB); David Portsmouth, Hampshire (GB)

(73) Assignee: Covidien AG, Neuhausen (CH)

( * ) Notice: Subject to any disclaimer, the term of this patent is extended or adjusted under 35 U.S.C. 154(b) by 0 days.

(21) Appl. No.: 14/021,566

(22) Filed: Sep. 9, 2013

(65) Prior Publication Data

US 2014/0166184 A1    Jun. 19, 2014

Related U.S. Application Data

(62) Division of application No. 11/996,995, filed as application No. PCT/GB2006/002674 on Jul. 19, 2006, now Pat. No. 8,539,647.

(30) Foreign Application Priority Data

Jul. 26, 2005  (GB) .................................... 0515294.7

(51) Int. Cl.
*A61F 5/00* (2006.01)
*A41F 1/00* (2006.01)
(Continued)

(52) U.S. Cl.
CPC .............. *A41F 1/00* (2013.01); *A61F 13/0269* (2013.01); *A61F 13/0283* (2013.01); *A61F 13/041* (2013.01); *A61F 13/064* (2013.01); *A61F 13/065* (2013.01); *A61F 13/085* (2013.01); *A61F 13/581* (2013.01);
(Continued)

(58) Field of Classification Search
CPC    A61F 13/085; A61F 13/0269; A61F 13/0283
USPC ........................................................... 156/66
See application file for complete search history.

(56) References Cited

U.S. PATENT DOCUMENTS

| 908,959 A | 1/1909 | Cooke |
| 910,689 A | 1/1909 | Kelly et al. |

(Continued)

FOREIGN PATENT DOCUMENTS

| CA | 2582678 A1 | 4/2006 |
| CN | 1009155 A | 1/1987 |

(Continued)

OTHER PUBLICATIONS

Mittelman, Jonathan S., MD: "Effectiveness of Leg Compression in Preventing Venous Stasis", The American Journal of Surgery, Dec. 1982, p. 611-613, vol. 144, No. 6, Elsevier Publ., Bridgewater, NJ, USA.

(Continued)

*Primary Examiner* — Jeff Aftergut
*Assistant Examiner* — Jaeyun Lee

(57) ABSTRACT

A limited durability fastening for a garment. The garment is provided with fastening members which engage to close the fastening and the fastening members are provided with means for controlling the degradation of the closure strength of the fastening as it is opened and closed and thus the number of permissible closures of the fastening having a pre-determined closure strength. The garment is particularly useful when fitted to a foot where short life is desirable at low cost or to a garment where re-use is to be discouraged for either clinical or commercial reasons.

8 Claims, 27 Drawing Sheets

(51) Int. Cl.
  *A61F 13/02* (2006.01)
  *A61F 13/04* (2006.01)
  *A61F 13/06* (2006.01)
  *A61F 13/58* (2006.01)
  *A61H 9/00* (2006.01)
  *A61F 13/08* (2006.01)
  *A61F 13/00* (2006.01)
  *A61F 13/84* (2006.01)

(52) U.S. Cl.
  CPC ....... *A61H 9/0078* (2013.01); *A41D 2300/328* (2013.01); *A61F 13/08* (2013.01); *A61F 2013/0028* (2013.01); *A61F 2013/00174* (2013.01); *A61F 2013/8497* (2013.01); *A61H 2201/1697* (2013.01); *A61H 2205/10* (2013.01); *Y10T 24/33* (2015.01)

(56) References Cited

U.S. PATENT DOCUMENTS

| | | |
|---|---|---|
| 1,510,482 A | 10/1924 | Kramer |
| 1,608,239 A | 11/1926 | Rosett |
| 2,199,408 A | 5/1940 | Liberte |
| 2,250,617 A | 7/1941 | Argentin |
| 2,489,388 A | 11/1949 | Rubin |
| 2,533,504 A | 12/1950 | Poor |
| 2,638,915 A | 5/1953 | Mitchell |
| 2,676,587 A | 4/1954 | Corcoran |
| 2,694,395 A | 11/1954 | Brown |
| 2,853,998 A | 9/1958 | Emerson |
| 2,880,721 A | 4/1959 | Corcoran |
| 2,896,612 A | 7/1959 | Bates et al. |
| 2,998,817 A | 9/1961 | Armstrong |
| 3,164,152 A | 1/1965 | Nicoll |
| 3,245,405 A | 4/1966 | Gardner |
| 3,288,132 A | 11/1966 | Meredith |
| 3,351,055 A | 11/1967 | Gottfried |
| 3,454,010 A | 7/1969 | Lilligren et al. |
| 3,469,769 A | 9/1969 | Guenther |
| 3,473,527 A | 10/1969 | Spiro |
| 3,504,675 A | 4/1970 | Bishop, Jr. |
| 3,561,435 A | 2/1971 | Nicholson |
| 3,568,227 A | 3/1971 | Dunham |
| 3,606,880 A | 9/1971 | Ogle, Jr. |
| 3,638,334 A | 2/1972 | Malikowski |
| 3,701,173 A | 10/1972 | Whitney |
| 3,728,875 A | 4/1973 | Hartigan et al. |
| 3,760,795 A | 9/1973 | Adelhed |
| 3,770,040 A | 11/1973 | De Cicco |
| 3,771,519 A | 11/1973 | Haake |
| 3,786,805 A | 1/1974 | Tourin |
| 3,824,992 A | 7/1974 | Nicholson et al. |
| 3,826,249 A | 7/1974 | Lee et al. |
| 3,862,629 A | 1/1975 | Rotta |
| 3,868,952 A | 3/1975 | Hatton |
| 3,877,426 A | 4/1975 | Nirschl |
| 3,878,839 A | 4/1975 | Norton et al. |
| 3,899,210 A | 8/1975 | Samhammer et al. |
| 3,901,221 A | 8/1975 | Nicholson et al. |
| 3,906,937 A | 9/1975 | Aronson |
| 3,920,006 A | 11/1975 | Lapidus |
| D239,981 S | 5/1976 | Arluck et al. |
| 3,955,565 A | 5/1976 | Johnson, Jr. |
| 4,013,069 A | 3/1977 | Hasty |
| 4,029,087 A | 6/1977 | Dye et al. |
| 4,030,488 A | 6/1977 | Hasty |
| 4,054,129 A | 10/1977 | Byars et al. |
| 4,066,084 A | 1/1978 | Tillander |
| 4,076,022 A | 2/1978 | Walker |
| 4,091,804 A | 5/1978 | Hasty |
| 4,116,236 A | 9/1978 | Albert |
| 4,146,021 A | 3/1979 | Brosseau et al. |
| 4,149,529 A | 4/1979 | Copeland et al. |
| 4,149,541 A | 4/1979 | Gammons et al. |
| 4,153,050 A | 5/1979 | Bishop et al. |
| 4,156,425 A | 5/1979 | Arkans |
| 4,197,837 A | 4/1980 | Tringali et al. |
| 4,198,961 A | 4/1980 | Arkans |
| 4,201,203 A | 5/1980 | Applegate |
| 4,202,312 A | 5/1980 | Mori et al. |
| 4,202,325 A | 5/1980 | Villari et al. |
| 4,206,751 A | 6/1980 | Schneider |
| 4,207,875 A | 6/1980 | Arkans |
| 4,207,876 A | 6/1980 | Annis |
| 4,219,892 A | 9/1980 | Rigdon |
| 4,253,449 A | 3/1981 | Arkans et al. |
| D259,058 S | 4/1981 | Marshall |
| 4,267,611 A | 5/1981 | Agulnick |
| 4,270,527 A | 6/1981 | Peters et al. |
| 4,280,485 A | 7/1981 | Arkans |
| 4,294,238 A | 10/1981 | Woodford |
| 4,294,240 A | 10/1981 | Thill |
| 4,300,245 A | 11/1981 | Saunders |
| 4,308,862 A | 1/1982 | Kalmar |
| 4,311,135 A | 1/1982 | Brueckner et al. |
| 4,320,746 A | 3/1982 | Arkans et al. |
| 4,343,302 A | 8/1982 | Dillon |
| 4,351,872 A | 9/1982 | Brosseau et al. |
| 4,352,253 A | 10/1982 | Oswalt |
| 4,355,632 A | 10/1982 | Sandman |
| 4,363,125 A | 12/1982 | Brewer et al. |
| 4,372,297 A | 2/1983 | Perlin |
| 4,375,217 A | 3/1983 | Arkans et al. |
| 4,379,217 A | 4/1983 | Youmans |
| 4,402,312 A | 9/1983 | Villari et al. |
| 4,408,599 A | 10/1983 | Mummert |
| 4,417,587 A | 11/1983 | Ichinomiya et al. |
| 4,425,912 A | 1/1984 | Harper |
| 4,437,269 A | 3/1984 | Shaw |
| 4,442,834 A | 4/1984 | Tucker et al. |
| 4,445,505 A | 5/1984 | Labour et al. |
| 4,453,538 A | 6/1984 | Whitney |
| 4,522,197 A | 6/1985 | Hasegawa |
| 4,531,516 A | 7/1985 | Poole et al. |
| 4,547,906 A | 10/1985 | Nishida et al. |
| 4,547,919 A | 10/1985 | Wang |
| 4,552,821 A | 11/1985 | Gibbard et al. |
| 4,580,816 A | 4/1986 | Campbell et al. |
| 4,583,255 A | 4/1986 | Mogaki et al. |
| 4,593,692 A | 6/1986 | Flowers |
| 4,597,384 A | 7/1986 | Whitney |
| 4,614,179 A | 9/1986 | Gardner et al. |
| 4,614,180 A | 9/1986 | Gardner et al. |
| 4,624,244 A | 11/1986 | Taheri |
| 4,624,248 A | 11/1986 | Poole et al. |
| 4,650,452 A | 3/1987 | Jensen |
| 4,657,003 A | 4/1987 | Wirtz |
| 4,682,588 A | 7/1987 | Curlee |
| 4,696,289 A | 9/1987 | Gardner et al. |
| 4,699,424 A | 10/1987 | Andres et al. |
| 4,702,232 A | 10/1987 | Gardner et al. |
| 4,703,750 A | 11/1987 | Sebastian et al. |
| 4,706,658 A | 11/1987 | Cronin |
| 4,721,101 A | 1/1988 | Gardner et al. |
| 4,722,332 A | 2/1988 | Saggers |
| 4,730,606 A | 3/1988 | Leininger |
| 4,753,649 A * | 6/1988 | Pazdernik ............... 604/389 |
| 4,762,121 A | 8/1988 | Shienfeld |
| 4,773,397 A | 9/1988 | Wright et al. |
| 4,805,620 A | 2/1989 | Meistrell |
| 4,809,684 A | 3/1989 | Gardner et al. |
| 4,827,912 A | 5/1989 | Carrington et al. |
| 4,832,010 A | 5/1989 | Lerman |
| RE32,939 E | 6/1989 | Gardner et al. |
| RE32,940 E | 6/1989 | Gardner et al. |
| 4,836,194 A | 6/1989 | Sebastian et al. |
| 4,836,691 A | 6/1989 | Suzuki et al. |
| 4,841,956 A | 6/1989 | Gardner et al. |
| D302,301 S | 7/1989 | Robinette-Lehman |
| 4,846,160 A | 7/1989 | Gardner et al. |
| 4,846,189 A | 7/1989 | Sun |
| 4,869,265 A | 9/1989 | McEwen |
| 4,872,448 A | 10/1989 | Johnson, Jr. |

(56) References Cited

U.S. PATENT DOCUMENTS

| | | | |
|---|---|---|---|
| 4,876,788 A | 10/1989 | Steer et al. | |
| 4,883,073 A | 11/1989 | Aziz | |
| 4,886,053 A | 12/1989 | Neal | |
| 4,898,160 A | 2/1990 | Brownlee | |
| 4,913,136 A | 4/1990 | Chong et al. | |
| 4,938,207 A | 7/1990 | Vargo | |
| 4,938,208 A | 7/1990 | Dye | |
| 4,938,226 A | 7/1990 | Danielsson et al. | |
| 4,945,571 A | 8/1990 | Calvert | |
| 4,947,834 A | 8/1990 | Kartheus et al. | |
| 4,957,105 A | 9/1990 | Kurth | |
| 4,960,115 A | 10/1990 | Ranciato | |
| 4,964,402 A | 10/1990 | Grim et al. | |
| 4,979,953 A | 12/1990 | Spence | |
| 4,985,024 A | 1/1991 | Sipinen | |
| 4,989,273 A | 2/1991 | Cromartie | |
| 4,997,452 A | 3/1991 | Kovach et al. | |
| 5,007,411 A | 4/1991 | Dye | |
| 5,014,681 A | 5/1991 | Neeman et al. | |
| 5,022,387 A | 6/1991 | Hasty | |
| 5,031,604 A | 7/1991 | Dye | |
| 5,048,536 A | 9/1991 | McEwen | |
| 5,052,377 A | 10/1991 | Frajdenrajch | |
| 5,062,414 A | 11/1991 | Grim | |
| 5,069,219 A | 12/1991 | Knoblich | |
| 5,071,415 A | 12/1991 | Takemoto | |
| 5,080,951 A | 1/1992 | Guthrie | |
| 5,082,284 A | 1/1992 | Reed | |
| 5,109,832 A | 5/1992 | Proctor et al. | |
| 5,117,812 A | 6/1992 | McWhorter | |
| 5,120,300 A | 6/1992 | Shaw | |
| 5,135,473 A | 8/1992 | Epler et al. | |
| 5,139,475 A | 8/1992 | Robicsek | |
| 5,139,476 A | 8/1992 | Peters | |
| 5,139,479 A | 8/1992 | Peters | |
| 5,146,932 A | 9/1992 | McCabe | |
| 5,156,629 A | 10/1992 | Shane et al. | |
| 5,158,541 A | 10/1992 | McCurley | |
| 5,168,576 A | 12/1992 | Krent et al. | |
| 5,172,689 A | 12/1992 | Wright | |
| D332,495 S | 1/1993 | Lake | |
| 5,179,941 A | 1/1993 | Siemssen et al. | |
| 5,181,522 A | 1/1993 | McEwen | |
| 5,186,163 A | 2/1993 | Dye | |
| 5,193,549 A | 3/1993 | Bellin et al. | |
| 5,211,162 A | 5/1993 | Gillen, Jr. et al. | |
| 5,226,245 A | 7/1993 | Lamont | |
| 5,226,564 A | 7/1993 | Steer et al. | |
| 5,228,478 A | 7/1993 | Kleisle | |
| 5,230,335 A | 7/1993 | Johnson, Jr. et al. | |
| 5,245,990 A | 9/1993 | Bertinin | |
| 5,259,397 A | 11/1993 | McCabe | |
| 5,261,871 A | 11/1993 | Greenfield | |
| 5,263,473 A | 11/1993 | McWhorter | |
| 5,275,588 A * | 1/1994 | Matsumoto et al. | 604/372 |
| 5,277,695 A | 1/1994 | Johnson, Jr. et al. | |
| 5,277,697 A | 1/1994 | France et al. | |
| 5,288,286 A | 2/1994 | Davis | |
| 5,312,431 A | 5/1994 | McEwen | |
| 5,314,455 A | 5/1994 | Johnson, Jr. et al. | |
| 5,334,135 A | 8/1994 | Grim et al. | |
| 5,342,285 A | 8/1994 | Dye | |
| 5,354,260 A | 10/1994 | Cook | |
| 5,378,224 A | 1/1995 | Billotti | |
| 5,383,894 A | 1/1995 | Dye | |
| 5,383,919 A | 1/1995 | Kelly et al. | |
| 5,385,538 A | 1/1995 | Mann | |
| 5,389,065 A | 2/1995 | Johnson, Jr. | |
| 5,391,141 A | 2/1995 | Hamilton | |
| 5,399,153 A | 3/1995 | Caprio, Jr. et al. | |
| 5,403,265 A | 4/1995 | Berguer et al. | |
| 5,406,661 A | 4/1995 | Pekar | |
| 5,407,421 A | 4/1995 | Goldsmith | |
| D358,216 S | 5/1995 | Dye | |
| 5,413,142 A | 5/1995 | Johnson et al. | |
| 5,413,582 A | 5/1995 | Eaton | |
| 5,419,757 A | 5/1995 | Daneshvar | |
| 5,425,701 A | 6/1995 | Oster et al. | |
| 5,435,009 A | 7/1995 | Schild et al. | |
| 5,437,595 A | 8/1995 | Smith | |
| 5,437,610 A | 8/1995 | Cariapa et al. | |
| 5,441,533 A | 8/1995 | Johnson et al. | |
| 5,443,440 A | 8/1995 | Tumey et al. | |
| 5,449,341 A | 9/1995 | Harris | |
| 5,449,379 A | 9/1995 | Hadtke | |
| 5,450,858 A | 9/1995 | Zablotsky et al. | |
| 5,451,201 A | 9/1995 | Prengler | |
| 5,453,081 A | 9/1995 | Hansen | |
| 5,455,969 A | 10/1995 | Pratson et al. | |
| 5,458,265 A | 10/1995 | Hester et al. | |
| 5,462,517 A | 10/1995 | Mann | |
| 5,466,250 A | 11/1995 | Johnson, Jr. et al. | |
| 5,470,156 A | 11/1995 | May | |
| 5,478,119 A | 12/1995 | Dye | |
| 5,489,252 A | 2/1996 | May | |
| 5,489,259 A | 2/1996 | Jacobs et al. | |
| 5,496,262 A | 3/1996 | Johnson, Jr. et al. | |
| 5,503,620 A | 4/1996 | Danzger | |
| 5,511,552 A | 4/1996 | Johnson | |
| 5,513,658 A | 5/1996 | Goseki | |
| 5,514,081 A | 5/1996 | Mann | |
| 5,514,155 A | 5/1996 | Daneshvar | |
| 5,527,267 A | 6/1996 | Billotti | |
| 5,554,105 A | 9/1996 | Taylor | |
| D376,013 S | 11/1996 | Sandman et al. | |
| 5,575,762 A | 11/1996 | Peeler et al. | |
| 5,578,055 A | 11/1996 | McEwen | |
| 5,584,798 A | 12/1996 | Fox | |
| 5,588,954 A | 12/1996 | Ribando et al. | |
| 5,588,955 A | 12/1996 | Johnson, Jr. et al. | |
| 5,588,956 A | 12/1996 | Billotti | |
| 5,591,200 A | 1/1997 | Cone et al. | |
| 5,591,337 A | 1/1997 | Lynn et al. | |
| 5,603,690 A | 2/1997 | Barry | |
| 5,609,570 A | 3/1997 | Lamont | |
| 5,620,411 A | 4/1997 | Schumann et al. | |
| 5,622,113 A | 4/1997 | Hansen | |
| 5,626,556 A | 5/1997 | Tobler et al. | |
| 5,626,557 A | 5/1997 | Mann | |
| 5,634,889 A | 6/1997 | Gardner et al. | |
| 5,637,106 A | 6/1997 | Mitchell et al. | |
| 5,640,714 A | 6/1997 | Tanaka | |
| 5,649,954 A | 7/1997 | McEwen | |
| 5,653,244 A | 8/1997 | Shaw | |
| D383,547 S | 9/1997 | Mason et al. | |
| 5,664,270 A | 9/1997 | Bell et al. | |
| 5,669,872 A | 9/1997 | Fox | |
| 5,673,028 A | 9/1997 | Levy | |
| 5,674,262 A | 10/1997 | Tumey | |
| 5,678,558 A | 10/1997 | Johnson | |
| 5,695,453 A | 12/1997 | Neal | |
| 5,704,999 A | 1/1998 | Lukich et al. | |
| 5,711,757 A | 1/1998 | Bryant | |
| 5,711,760 A | 1/1998 | Ibrahim et al. | |
| 5,717,996 A | 2/1998 | Feldmann | |
| 5,720,739 A | 2/1998 | Hilston et al. | |
| 5,725,485 A | 3/1998 | Ribando et al. | |
| 5,728,055 A | 3/1998 | Sebastian | |
| 5,728,057 A | 3/1998 | Ouellette et al. | |
| 5,730,710 A | 3/1998 | Eichhorn et al. | |
| 5,733,304 A | 3/1998 | Spence | |
| 5,741,295 A | 4/1998 | McEwen | |
| 5,746,213 A | 5/1998 | Marks | |
| 5,759,167 A | 6/1998 | Shields et al. | |
| 5,765,298 A | 6/1998 | Potter et al. | |
| 5,769,800 A | 6/1998 | Gelfand et al. | |
| 5,769,801 A | 6/1998 | Tumey et al. | |
| 5,772,880 A | 6/1998 | Lynn et al. | |
| 5,790,998 A | 8/1998 | Crescimbeni | |
| 5,795,312 A | 8/1998 | Dye | |
| 5,797,851 A | 8/1998 | Byrd | |
| 5,823,981 A | 10/1998 | Grim et al. | |
| 5,830,164 A | 11/1998 | Cone et al. | |
| 5,833,639 A | 11/1998 | Nunes et al. | |

(56) References Cited

U.S. PATENT DOCUMENTS

| | | |
|---|---|---|
| 5,840,049 A | 11/1998 | Tumey et al. |
| 5,843,007 A | 12/1998 | McEwen et al. |
| D403,775 S | 1/1999 | Davis et al. |
| D405,884 S | 2/1999 | Roper |
| 5,876,359 A | 3/1999 | Bock et al. |
| 5,891,065 A | 4/1999 | Cariapa et al. |
| 5,894,682 A | 4/1999 | Broz |
| D411,301 S | 6/1999 | Hampson et al. |
| 5,916,183 A | 6/1999 | Reid |
| 5,925,010 A | 7/1999 | Caprio, Jr. |
| 5,926,850 A | 7/1999 | Han |
| 5,931,797 A | 8/1999 | Tumey et al. |
| 5,938,628 A | 8/1999 | Oguri et al. |
| 5,951,502 A | 9/1999 | Peeler et al. |
| 5,957,872 A | 9/1999 | Flick |
| 5,966,763 A | 10/1999 | Thomas et al. |
| 5,968,072 A | 10/1999 | Hite et al. |
| 5,970,519 A | 10/1999 | Weber |
| 5,976,099 A | 11/1999 | Kellogg |
| 5,976,300 A | 11/1999 | Buchanan et al. |
| 5,988,704 A | 11/1999 | Ryhman |
| 5,989,204 A | 11/1999 | Lina |
| 5,991,654 A | 11/1999 | Tumey et al. |
| 5,997,495 A | 12/1999 | Cook et al. |
| 5,997,981 A | 12/1999 | McCormack et al. |
| 6,001,119 A | 12/1999 | Hampson et al. |
| 6,007,559 A | 12/1999 | Arkans |
| 6,010,471 A | 1/2000 | Ben-Noon |
| 6,021,780 A | 2/2000 | Darby |
| 6,036,718 A | 3/2000 | Ledford et al. |
| 6,048,326 A | 4/2000 | Davis et al. |
| 6,051,016 A | 4/2000 | Mesaros et al. |
| 6,056,713 A | 5/2000 | Hayashi |
| 6,062,244 A | 5/2000 | Arkans |
| 6,066,217 A | 5/2000 | Dibble et al. |
| 6,076,193 A | 6/2000 | Hood |
| 6,080,120 A | 6/2000 | Sandman et al. |
| D428,153 S | 7/2000 | Davis |
| 6,110,135 A | 8/2000 | Madow et al. |
| 6,120,469 A | 9/2000 | Bruder |
| 6,126,683 A | 10/2000 | Momtaheni |
| 6,129,688 A | 10/2000 | Arkans |
| 6,129,695 A | 10/2000 | Peters et al. |
| 6,134,720 A | 10/2000 | Foreman |
| 6,135,116 A | 10/2000 | Vogel et al. |
| 6,145,143 A | 11/2000 | Hicks et al. |
| 6,149,600 A | 11/2000 | Poorman-Ketchum |
| 6,149,616 A | 11/2000 | Szlema et al. |
| 6,152,495 A | 11/2000 | Hoffmann et al. |
| 6,152,893 A | 11/2000 | Pigg et al. |
| 6,168,539 B1 | 1/2001 | Maina |
| 6,171,271 B1 | 1/2001 | Hörnberg |
| 6,179,796 B1 | 1/2001 | Waldridge |
| 6,197,045 B1 | 3/2001 | Carson |
| 6,203,510 B1 | 3/2001 | Takeuchi et al. |
| 6,209,159 B1 | 4/2001 | Murphy |
| 6,212,719 B1 | 4/2001 | Thomas et al. |
| 6,227,275 B1 | 5/2001 | Dibble et al. |
| 6,231,507 B1 | 5/2001 | Zikorus et al. |
| 6,231,532 B1 | 5/2001 | Watson et al. |
| 6,245,023 B1 | 6/2001 | Clemmons |
| 6,254,554 B1 | 7/2001 | Turtzo |
| 6,257,626 B1 | 7/2001 | Campau |
| 6,257,627 B1 | 7/2001 | Fujiwara et al. |
| 6,260,201 B1 | 7/2001 | Rankin |
| 6,273,866 B2 | 8/2001 | Thomas et al. |
| 6,290,662 B1 | 9/2001 | Morris et al. |
| 6,290,664 B1 | 9/2001 | Nauert |
| 6,296,617 B1 | 10/2001 | Peeler et al. |
| 6,315,745 B1 | 11/2001 | Kloecker |
| 6,319,215 B1 | 11/2001 | Manor et al. |
| 6,322,530 B1 | 11/2001 | Johnson, Jr. et al. |
| 6,336,935 B1 | 1/2002 | Davis et al. |
| 6,338,723 B1 | 1/2002 | Carpenter et al. |
| 6,349,506 B1 | 2/2002 | Pace et al. |
| 6,358,219 B1 | 3/2002 | Arkans |
| 6,361,496 B1 | 3/2002 | Zikorus et al. |
| 6,368,357 B1 | 4/2002 | Schon et al. |
| 6,375,633 B1 | 4/2002 | Endress et al. |
| 6,385,778 B1 | 5/2002 | Johnson |
| 6,385,864 B1 | 5/2002 | Sell, Jr. et al. |
| 6,387,065 B1 | 5/2002 | Tumey |
| 6,402,879 B1 | 6/2002 | Tawney et al. |
| 6,409,691 B1 | 6/2002 | Dakin et al. |
| 6,421,859 B1 | 7/2002 | Hicks et al. |
| 6,423,053 B1 | 7/2002 | Lee |
| 6,436,064 B1 | 8/2002 | Kloecker |
| 6,440,093 B1 | 8/2002 | McEwen et al. |
| 6,447,460 B1 | 9/2002 | Zheng et al. |
| 6,447,467 B1 | 9/2002 | Barak |
| 6,463,934 B1 | 10/2002 | Johnson, Jr. et al. |
| 6,468,237 B1 | 10/2002 | Lina |
| 6,478,757 B1 | 11/2002 | Barak |
| 6,478,761 B2 | 11/2002 | Bracamonte-Sommer |
| 6,488,643 B1 | 12/2002 | Tumey et al. |
| 6,493,568 B1 | 12/2002 | Bell et al. |
| 6,494,852 B1 | 12/2002 | Barak et al. |
| 6,508,205 B1 | 1/2003 | Zink |
| 6,520,926 B2 | 2/2003 | Hall |
| 6,526,597 B1 | 3/2003 | Shepard |
| 6,527,727 B2 | 3/2003 | Itonaga et al. |
| 6,537,298 B2 | 3/2003 | Dedo |
| 6,540,707 B1 | 4/2003 | Stark et al. |
| 6,544,202 B2 | 4/2003 | McEwen et al. |
| 6,549,748 B2 | 4/2003 | Miura |
| 6,551,280 B1 | 4/2003 | Knighton et al. |
| 6,554,785 B1 | 4/2003 | Sroufe et al. |
| 6,557,704 B1 | 5/2003 | Randolph |
| 6,558,338 B1 | 5/2003 | Wasserman |
| 6,562,060 B1 | 5/2003 | Momtaheni |
| 6,589,267 B1 | 7/2003 | Hui |
| 6,589,534 B1 | 7/2003 | Shaul et al. |
| 6,592,534 B1 | 7/2003 | Rutt et al. |
| 6,593,508 B1 | 7/2003 | Harder |
| 6,598,249 B2 | 7/2003 | Pajanacci et al. |
| D478,995 S | 8/2003 | Cipra et al. |
| 6,616,622 B1 | 9/2003 | Barberio |
| 6,618,859 B1 | 9/2003 | Kadymir et al. |
| 6,629,941 B1 | 10/2003 | Ishibashi et al. |
| 6,645,165 B2 | 11/2003 | Waldridge et al. |
| D484,986 S | 1/2004 | Cipra et al. |
| 6,676,614 B1 | 1/2004 | Hansen et al. |
| 6,682,547 B2 | 1/2004 | McEwen et al. |
| 6,685,661 B2 | 2/2004 | Peled |
| 6,719,711 B1 | 4/2004 | Islava |
| 6,726,641 B2 | 4/2004 | Chiang et al. |
| 6,746,470 B2 | 6/2004 | McEwen et al. |
| 6,757,516 B2 | 6/2004 | Miura |
| 6,762,337 B2 | 7/2004 | Boukanov et al. |
| 6,762,338 B2 | 7/2004 | Harder |
| 6,842,915 B2 | 1/2005 | Turner et al. |
| 6,846,294 B2 | 1/2005 | Rastegar et al. |
| 6,846,295 B1 | 1/2005 | Ben-Nun |
| 6,849,057 B2 | 2/2005 | Satou et al. |
| 6,852,089 B2 | 2/2005 | Kloecker et al. |
| 6,860,862 B2 | 3/2005 | Waldridge et al. |
| 6,862,989 B2 | 3/2005 | Belanger et al. |
| 6,866,636 B2 | 3/2005 | Inoue et al. |
| 6,869,409 B2 | 3/2005 | Rothman et al. |
| D506,553 S | 6/2005 | Tesluk |
| 6,945,944 B2 | 9/2005 | Kuiper et al. |
| D510,626 S | 10/2005 | Krahner et al. |
| 6,966,884 B2 | 11/2005 | Waldridge et al. |
| 6,973,690 B2 | 12/2005 | Muci et al. |
| 6,984,215 B2 | 1/2006 | Shah et al. |
| 6,991,613 B2 | 1/2006 | Sensabaugh |
| 7,011,640 B2 | 3/2006 | Patterson et al. |
| 7,022,096 B1 | 4/2006 | Alfieri |
| 7,041,074 B1 | 5/2006 | Averianov et al. |
| 7,044,924 B1 | 5/2006 | Roth et al. |
| 7,048,703 B2 | 5/2006 | Riach |
| 7,063,676 B2 | 6/2006 | Barak et al. |
| 7,090,500 B1 | 8/2006 | Guttman |
| 7,104,967 B2 | 9/2006 | Rothman et al. |

(56) References Cited

U.S. PATENT DOCUMENTS

| | | |
|---|---|---|
| D533,668 S | 12/2006 | Brown |
| 7,166,077 B2 | 1/2007 | Millay et al. |
| 7,214,202 B1 | 5/2007 | Vogel et al. |
| 7,217,249 B2 | 5/2007 | Scott |
| D545,972 S | 7/2007 | Wieringa et al. |
| 7,237,272 B2 | 7/2007 | Botcher |
| 7,238,080 B2 | 7/2007 | Gimble |
| 7,244,483 B2 | 7/2007 | Tawney et al. |
| 7,258,676 B2 | 8/2007 | Calderon et al. |
| D550,367 S | 9/2007 | Nash |
| 7,276,037 B2 | 10/2007 | Ravikumar |
| 7,276,039 B2 | 10/2007 | Garelick et al. |
| 7,278,980 B1 | 10/2007 | Garelick et al. |
| 7,282,038 B2 | 10/2007 | Gillis et al. |
| 7,285,103 B2 | 10/2007 | Nathanson |
| 7,288,076 B2 | 10/2007 | Grim et al. |
| 7,297,128 B2 | 11/2007 | Binder et al. |
| 7,300,410 B1 | 11/2007 | Weber |
| 7,303,539 B2 | 12/2007 | Binder et al. |
| 7,306,568 B2 | 12/2007 | Diana |
| 7,310,847 B2 | 12/2007 | Bolkan et al. |
| 7,318,812 B2 | 1/2008 | Taylor et al. |
| D562,461 S | 2/2008 | Nash |
| D562,462 S | 2/2008 | Muir et al. |
| 7,326,227 B2 | 2/2008 | Dedo et al. |
| 7,329,232 B2 | 2/2008 | Lipshaw et al. |
| 7,351,217 B2 | 4/2008 | Scherpenborg |
| 7,353,770 B2 | 4/2008 | Sanguinetti |
| 7,354,410 B2 | 4/2008 | Perry et al. |
| 7,354,411 B2 | 4/2008 | Perry et al. |
| 7,374,550 B2 | 5/2008 | Hansen et al. |
| D577,124 S | 9/2008 | Freeland et al. |
| 7,424,936 B2 | 9/2008 | McClellan |
| 7,442,175 B2 | 10/2008 | Meyer et al. |
| D580,553 S | 11/2008 | Nash |
| 7,465,283 B2 | 12/2008 | Grim et al. |
| 7,468,048 B2 | 12/2008 | Meehan |
| 7,473,816 B2 | 1/2009 | Hall |
| D594,561 S | 6/2009 | Freeland et al. |
| 7,543,399 B2 | 6/2009 | Kilgore et al. |
| 7,556,707 B2 | 7/2009 | Giori |
| 7,559,908 B2 | 7/2009 | Ravikumar |
| 7,578,799 B2 | 8/2009 | Thorsteinsson et al. |
| 7,591,796 B1 | 9/2009 | Barak et al. |
| 7,591,797 B2 | 9/2009 | Hakonson et al. |
| 7,597,675 B2 | 10/2009 | Ingimundarson et al. |
| 7,615,027 B2 | 11/2009 | Nordt, III et al. |
| 7,618,384 B2 | 11/2009 | Nardi et al. |
| 7,618,389 B2 | 11/2009 | Nordt, III et al. |
| 7,625,348 B2 | 12/2009 | Young et al. |
| 7,637,879 B2 | 12/2009 | Barak et al. |
| D608,006 S | 1/2010 | Avitable et al. |
| 7,654,117 B2 | 2/2010 | Barnett |
| 7,670,306 B2 | 3/2010 | Nordt, III et al. |
| 7,691,084 B2 | 4/2010 | Knighton et al. |
| 7,748,090 B2 | 7/2010 | Seth et al. |
| 7,749,182 B2 | 7/2010 | Gramza et al. |
| 7,758,607 B2 | 7/2010 | McEwen et al. |
| 7,766,890 B2 | 8/2010 | Ito et al. |
| 7,771,376 B2 | 8/2010 | Roth et al. |
| 7,780,614 B2 | 8/2010 | Bruce et al. |
| 7,780,698 B2 | 8/2010 | McEwen et al. |
| 7,803,358 B2 | 9/2010 | Gordan et al. |
| 7,827,624 B1 | 11/2010 | Cole |
| 7,871,387 B2 | 1/2011 | Tordella et al. |
| 7,874,997 B2 | 1/2011 | Jaccard |
| 7,882,568 B2 | 2/2011 | Fee |
| 7,931,606 B2 | 4/2011 | Meyer |
| 7,967,766 B2 | 6/2011 | Ravikumar |
| 7,976,487 B2 | 7/2011 | Gramza et al. |
| 8,002,721 B2 | 8/2011 | Bretl et al. |
| 8,016,778 B2 | 9/2011 | Brown et al. |
| 8,016,779 B2 | 9/2011 | Brown et al. |
| 8,021,388 B2 | 9/2011 | Brown et al. |
| 8,029,450 B2 | 10/2011 | Brown et al. |
| 8,029,451 B2 | 10/2011 | Meyer et al. |
| 8,034,007 B2 | 10/2011 | Avitable et al. |
| 8,034,013 B2 | 10/2011 | Winkler |
| 8,070,699 B2 | 12/2011 | Avitable et al. |
| 8,109,892 B2 | 2/2012 | Brown et al. |
| 8,114,117 B2 | 2/2012 | Avitable |
| 8,128,584 B2 | 3/2012 | Brown |
| 8,177,734 B2 | 5/2012 | Vess |
| 8,235,923 B2 | 8/2012 | Avitable et al. |
| 8,419,666 B2 | 4/2013 | Liu et al. |
| 2001/0018564 A1 | 8/2001 | Manor et al. |
| 2002/0042585 A1 | 4/2002 | Kloecker |
| 2002/0068886 A1 | 6/2002 | Lin |
| 2002/0069731 A1 | 6/2002 | Soucy |
| 2002/0115949 A1 | 8/2002 | Kuslich et al. |
| 2002/0121235 A1 | 9/2002 | Carpenter et al. |
| 2003/0018313 A1 | 1/2003 | Tanzer et al. |
| 2003/0083605 A1 | 5/2003 | Edmund |
| 2003/0130644 A1* | 7/2003 | Baker ............................ 604/389 |
| 2003/0139255 A1 | 7/2003 | Lina |
| 2003/0199922 A1 | 10/2003 | Buckman |
| 2004/0010212 A1 | 1/2004 | Kuiper et al. |
| 2004/0039317 A1 | 2/2004 | Souney et al. |
| 2004/0039413 A1 | 2/2004 | Akerfeldt et al. |
| 2004/0054306 A1 | 3/2004 | Roth et al. |
| 2004/0068290 A1 | 4/2004 | Bates et al. |
| 2004/0097860 A1 | 5/2004 | Tauber |
| 2004/0158283 A1 | 8/2004 | Shook et al. |
| 2004/0158285 A1 | 8/2004 | Pillai |
| 2004/0176715 A1 | 9/2004 | Nelson |
| 2004/0181156 A1 | 9/2004 | Kingsford et al. |
| 2004/0181254 A1 | 9/2004 | Choi et al. |
| 2004/0199090 A1 | 10/2004 | Sanders et al. |
| 2004/0210167 A1 | 10/2004 | Webster |
| 2004/0236258 A1 | 11/2004 | Burns et al. |
| 2005/0070828 A1 | 3/2005 | Hampson et al. |
| 2005/0143683 A1 | 6/2005 | Waldridge et al. |
| 2005/0154336 A1 | 7/2005 | Kloecker et al. |
| 2005/0187503 A1 | 8/2005 | Tordella et al. |
| 2005/0209545 A1 | 9/2005 | Farrow et al. |
| 2005/0242315 A1 | 11/2005 | Lund |
| 2006/0010574 A1 | 1/2006 | Linnane et al. |
| 2006/0020236 A1 | 1/2006 | Ben-Nun |
| 2006/0026736 A1 | 2/2006 | Nordt et al. |
| 2006/0089617 A1* | 4/2006 | Bunnelle ....................... 604/389 |
| 2006/0102423 A1 | 5/2006 | Lang et al. |
| 2006/0135894 A1 | 6/2006 | Linnane et al. |
| 2006/0137072 A1 | 6/2006 | Visco et al. |
| 2006/0142719 A1 | 6/2006 | Vogt et al. |
| 2006/0161081 A1 | 7/2006 | Barak et al. |
| 2006/0189907 A1 | 8/2006 | Pick et al. |
| 2006/0211965 A1 | 9/2006 | Horn et al. |
| 2006/0287672 A1 | 12/2006 | McEwen et al. |
| 2006/0293151 A1 | 12/2006 | Rast |
| 2007/0038167 A1 | 2/2007 | Tabron et al. |
| 2007/0055188 A1 | 3/2007 | Avni et al. |
| 2007/0129658 A1 | 6/2007 | Hampson et al. |
| 2007/0130732 A1 | 6/2007 | Matsumura et al. |
| 2007/0135835 A1 | 6/2007 | McEwen et al. |
| 2007/0135836 A1 | 6/2007 | McEwen et al. |
| 2007/0179416 A1 | 8/2007 | Obrien et al. |
| 2007/0197947 A1 | 8/2007 | Scott |
| 2007/0260162 A1 | 11/2007 | Meyer et al. |
| 2007/0264497 A1* | 11/2007 | Kong ..................... 428/355 AC |
| 2007/0276310 A1 | 11/2007 | Lipshaw et al. |
| 2007/0276311 A1 | 11/2007 | Wieringa et al. |
| 2007/0282233 A1 | 12/2007 | Meyer et al. |
| 2008/0000477 A1 | 1/2008 | Huster et al. |
| 2008/0004555 A1 | 1/2008 | Reis et al. |
| 2008/0004560 A1 | 1/2008 | Miskie |
| 2008/0023423 A1 | 1/2008 | Duffy |
| 2008/0071204 A1 | 3/2008 | Linnane et al. |
| 2008/0072629 A1 | 3/2008 | Gehring |
| 2008/0082029 A1 | 4/2008 | Diana |
| 2008/0086071 A1 | 4/2008 | Weatherly |
| 2008/0087740 A1 | 4/2008 | Gusenoff et al. |
| 2008/0103397 A1 | 5/2008 | Barak |
| 2008/0103422 A1 | 5/2008 | Perry et al. |
| 2008/0141428 A1 | 6/2008 | Kapah et al. |

(56) References Cited

U.S. PATENT DOCUMENTS

| | | |
|---|---|---|
| 2008/0143007 A1 | 6/2008 | Tuma |
| 2008/0183115 A1 | 7/2008 | Pierce |
| 2008/0188786 A1 | 8/2008 | Hickling |
| 2008/0208092 A1 | 8/2008 | Sawa |
| 2008/0234615 A1 | 9/2008 | Cook et al. |
| 2008/0243173 A1 | 10/2008 | Thorpe |
| 2008/0245361 A1 | 10/2008 | Brown |
| 2008/0249440 A1 | 10/2008 | Avitable et al. |
| 2008/0249441 A1 | 10/2008 | Avitable et al. |
| 2008/0249443 A1 | 10/2008 | Avitable et al. |
| 2008/0249449 A1 | 10/2008 | Brown et al. |
| 2008/0249559 A1 | 10/2008 | Brown et al. |
| 2008/0250551 A1 | 10/2008 | Mazzarolo |
| 2008/0255485 A1 | 10/2008 | Johnson et al. |
| 2008/0281351 A1 | 11/2008 | Croushorn et al. |
| 2008/0306420 A1 | 12/2008 | Vess |
| 2008/0312682 A1 | 12/2008 | Shams et al. |
| 2009/0005718 A1 | 1/2009 | Lightbourne |
| 2009/0064919 A1 | 3/2009 | Greenwald |
| 2009/0082708 A1 | 3/2009 | Scott et al. |
| 2009/0099562 A1 | 4/2009 | Ingimudarson et al. |
| 2009/0110890 A1 | 4/2009 | Garza et al. |
| 2009/0124944 A1 | 5/2009 | Ravikumar |
| 2009/0133446 A1 | 5/2009 | Burrow et al. |
| 2009/0137938 A1 | 5/2009 | Parivash |
| 2009/0163842 A1 | 6/2009 | Cropper |
| 2009/0171223 A1 | 7/2009 | McEwen et al. |
| 2009/0198160 A1 | 8/2009 | Coyne |
| 2009/0198261 A1 | 8/2009 | Schweikert |
| 2009/0227917 A1 | 9/2009 | Nardi |
| 2009/0227919 A1 | 9/2009 | Nardi et al. |
| 2009/0227922 A1 | 9/2009 | Nardi et al. |
| 2009/0234265 A1 | 9/2009 | Reid, Jr. et al. |
| 2009/0270910 A1 | 10/2009 | Hargens et al. |
| 2009/0278707 A1 | 11/2009 | Biggins et al. |
| 2009/0281470 A1 | 11/2009 | Sandusky et al. |
| 2009/0299249 A1 | 12/2009 | Wilkes et al. |
| 2009/0312681 A1 | 12/2009 | McSpadden et al. |
| 2009/0320174 A1 | 12/2009 | Turner |
| 2009/0326576 A1 | 12/2009 | Ben-Nun |
| 2010/0004575 A1 | 1/2010 | Vess |
| 2010/0004676 A1 | 1/2010 | McEwen et al. |
| 2010/0010408 A1 | 1/2010 | Linares |
| 2010/0016771 A1 | 1/2010 | Arbesman et al. |
| 2010/0022930 A1 | 1/2010 | Koby et al. |
| 2010/0037369 A1 | 2/2010 | Reichert |
| 2010/0042026 A1 | 2/2010 | Kloecker et al. |
| 2010/0042028 A1 | 2/2010 | Frank et al. |
| 2010/0081974 A1 | 4/2010 | Vess |
| 2010/0081975 A1 | 4/2010 | Avitable et al. |
| 2010/0081977 A1 | 4/2010 | Vess |
| 2010/0210982 A1 | 8/2010 | Balachandran et al. |
| 2010/0268130 A1 | 10/2010 | Khan |
| 2012/0071801 A1 | 3/2012 | Avitable |
| 2012/0078146 A1 | 3/2012 | Deshpande |
| 2013/0184623 A1 | 7/2013 | Fraser |
| 2013/0310719 A1 | 11/2013 | Davis et al. |
| 2014/0236058 A1 | 8/2014 | Lee |

FOREIGN PATENT DOCUMENTS

| | | |
|---|---|---|
| DE | 19846922 A1 | 10/2011 |
| EP | 0221636 A1 | 5/1987 |
| EP | 0303029 A1 | 2/1989 |
| EP | 0408049 A2 | 1/1991 |
| EP | 0861651 A1 | 9/1998 |
| EP | 0893115 A2 | 1/1999 |
| EP | 1468816 A1 | 10/2004 |
| EP | 1980228 A2 | 10/2008 |
| FR | 2813770 A1 | 3/2002 |
| FR | 2950245 A1 | 9/2009 |
| GB | 2061086 A | 5/1981 |
| GB | 2178663 A | 2/1987 |
| GB | 2183483 A | 6/1987 |
| GB | 2313784 A | 12/1997 |
| GB | 2373444 A | 9/2002 |
| JP | 59218154 A | 12/1984 |
| JP | 60135110 U | 9/1985 |
| JP | 09262261 A | 10/1997 |
| JP | 2002065782 | 3/2002 |
| JP | 2003310312 A | 11/2003 |
| JP | 2004081709 | 3/2004 |
| JP | 2005066247 | 3/2005 |
| JP | 2009000277 A | 1/2009 |
| WO | 96/20685 A1 | 7/1996 |
| WO | 2004012644 A1 | 2/2004 |
| WO | 2004021950 A1 | 3/2004 |
| WO | 2005082315 A1 | 9/2005 |
| WO | 2006039242 A2 | 4/2006 |
| WO | 2006083865 A2 | 8/2006 |

OTHER PUBLICATIONS

Tyco Healthcare Kendall, SCD Response Catalog, Mar. 2000, pp. 1-2.

Tyco Healthcare Kendall, SCD Soft Sleeve Catalog, Apr. 2001, pp. 1-2.

The Kendall Company, Vascular Therapy Products Catalog, Jan. 1996, pp. 8-5 thru 8-7.

The Kendall Company, The New SCD Compression Sleeve, Aug. 1993, pp. 1-2.

Tyco Healthcare Kendall, Prevention Gets Personal Mar. 2001, pp. 1, 2, 4.

Kendall SCD, Sequential Compression Sleeves, Patent Information, Jan. 1993, 6 pgs.

Ramsley and Bushnell, "Development of the US Woodland Battle Dress Uniform", Jan. 1981, p. 8 paragraph 4.

Office action issued Nov. 18, 2010 regarding U.S. Appl. No. 12/242,268, 8 pgs.

Response filed Dec. 13, 2010 to Office Action dated Nov. 18, 2010 regarding U.S. Appl. No. 12/242,268, 5 pgs.

Office action issued Jan. 20, 2011 regarding U.S. Appl. No. 12/242,268, 14 pgs.

Response filed Apr. 19, 2011 to Office Action dated Jan. 20, 2011 regarding U.S. Appl. No. 12/242,268, 13 pgs.

Office action issued May 24, 2011 regarding U.S. Appl. No. 12/242,268, 15 pgs.

Response filed Aug. 24, 2011 to Office Action dated May 24, 2011 regarding U.S. Appl. No. 12/242,268, 8 pgs.

Office Action issued Sep. 13, 2011 from related Japanese Patent Application No. 2008-523432, 4 pgs (Translation).

Office action issued Nov. 8, 2012 in related U.S. Appl. No. 13/362,166, 8 pgs.

Response filed Feb. 8, 2013 to Office Action dated Nov. 8, 2012 regarding U.S. Appl. No. 13/362,166, 14 pgs.

Office action issued Dec. 3, 2012 in related U.S. Appl. No. 13/362,154, 10 pgs.

Response filed Mar. 4, 2013 to Office Action dated Dec. 3, 2012 regarding U.S. Appl. No. 13/362,154—14 pgs.

Office action issued Mar. 15, 2013 regarding U.S. Appl. No. 13/362,166, 13 pgs.

Response filed Jun. 14, 2013 to Office Action dated Mar. 15, 2013 regarding U.S. Appl. No. 13/362,166—13 pgs.

Office action issued Aug. 28, 2013 regarding U.S. Appl. No. 13/362,166, 13 pgs.

Response filed Nov. 27, 2013 to Office Action dated Aug. 28, 2013 regarding U.S. Appl. No. 13/362,166—12 pgs.

Office action issued Dec. 18, 2013 regarding U.S. Appl. No. 13/362,166, 14 pgs.

Office action issued Jun. 10, 2011 regarding Chinese Patent Application No. 200680035366.6, 8 pgs.

Office action issued Mar. 29, 2013 regarding U.S. Appl. No. 11/996,995, 8 pgs.

Response filed Jun. 28, 2013 to Office Action dated Mar. 29, 2013 regarding U.S. Appl. No. 11/996,995—7 pgs.

Chinese Office action issued Mar. 31, 2012 regarding Chinese Patent Application Serial No. 200680035366.6, 6 pgs.

(56) References Cited

OTHER PUBLICATIONS

Chinese Office action issued Nov. 5, 2012 regarding Chinese Patent Application Serial No. 200680035366.6, 4 pgs.
Japanese Office action issued Apr. 3, 2012 regarding Japanese Patent Application Serial No. 2008-523432, 2 pgs.
Office action issued Nov. 9, 2011 regarding U.S. Appl. No. 12/241,914, 9 pgs.
Response filed Jan. 12, 2012 to Office Action dated Nov. 9, 2011 regarding U.S. Appl. No. 12/241,914, 13 pgs.
Response filed Mar. 7, 2014 to Office action issued Dec. 18, 2013 in related U.S. Appl. No. 13/362,166, 9 pages.
Office action issued Feb. 12, 2015 in related U.S. Appl. No. 13/362,166, 19 pages.
Response filed May 11, 2015 to Office action issued Feb. 12, 2015 in related U.S. Appl. No. 13/362,166, 14 pages.
Office Action dated Sep. 28, 2014 in related Chinese application serial No. 201310159529.3, 13 pages.
Office action issued Jul. 15, 2015 in related U.S. Appl. No. 13/362,166, 16 pages.

* cited by examiner

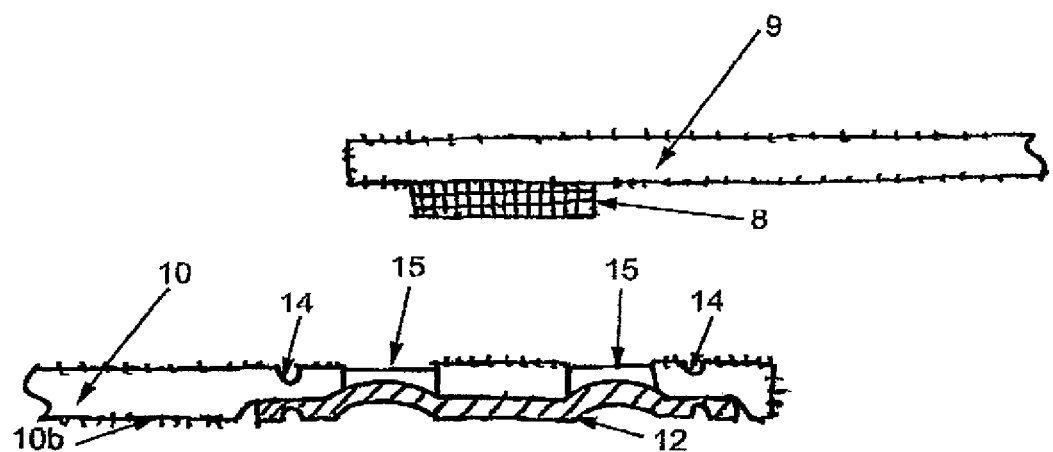

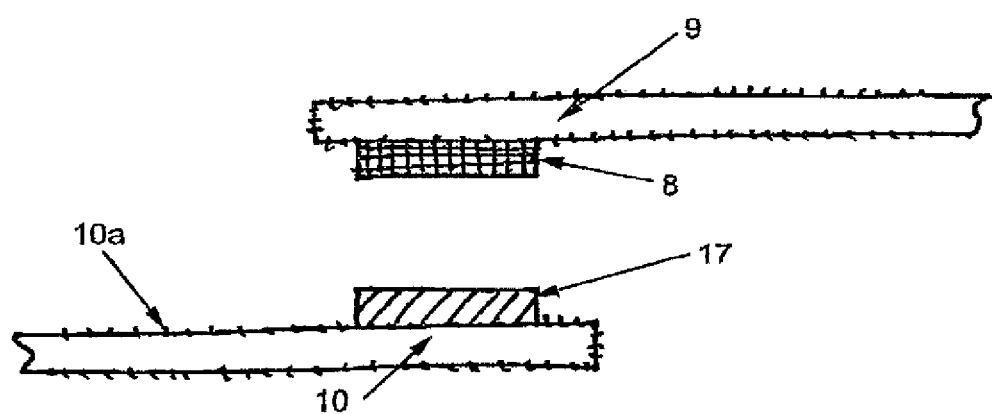

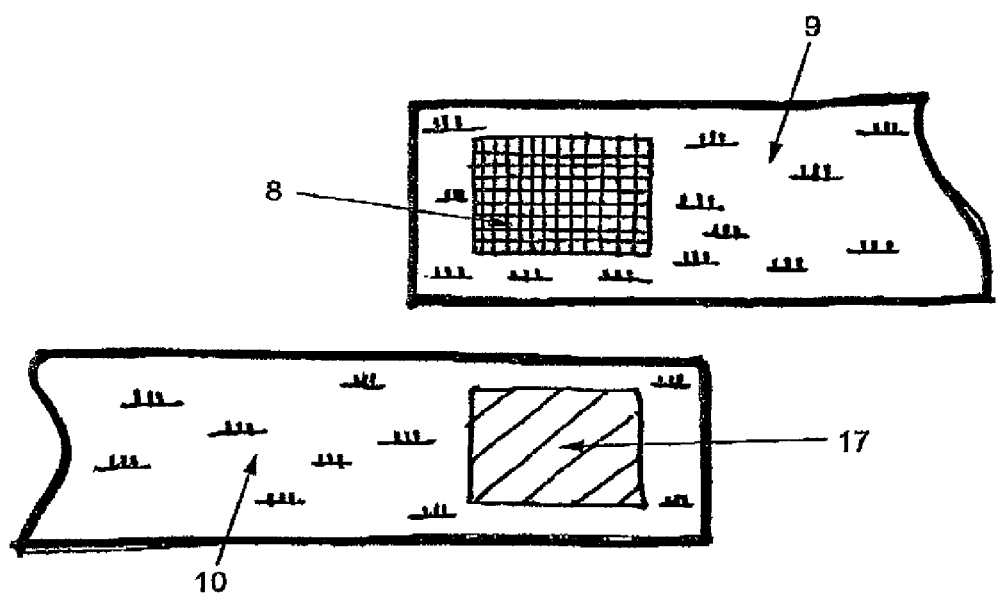

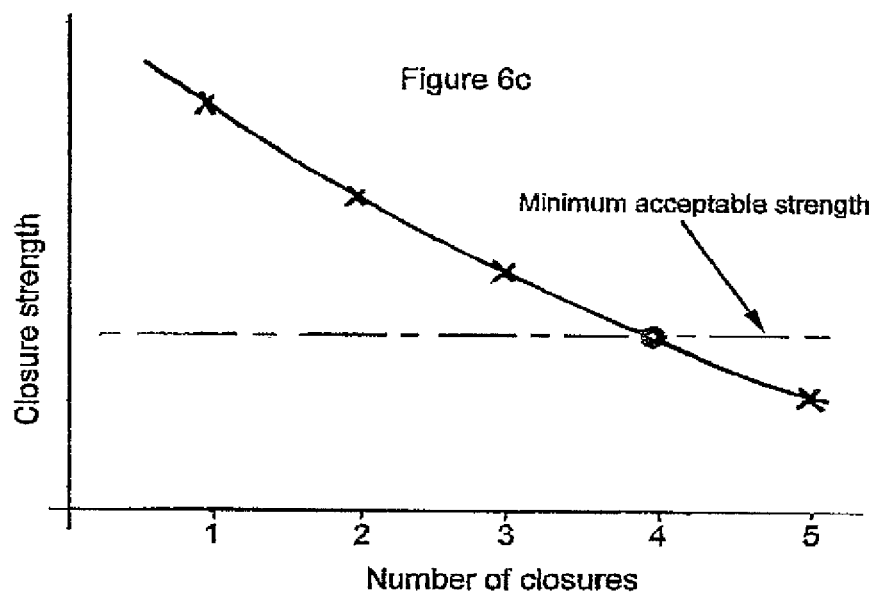

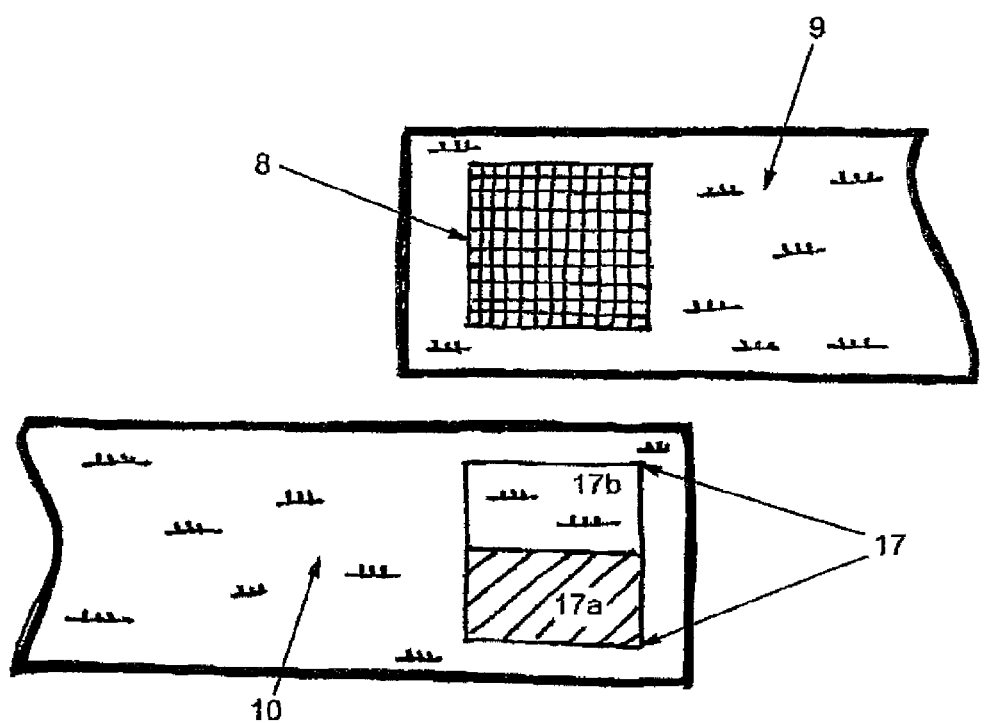

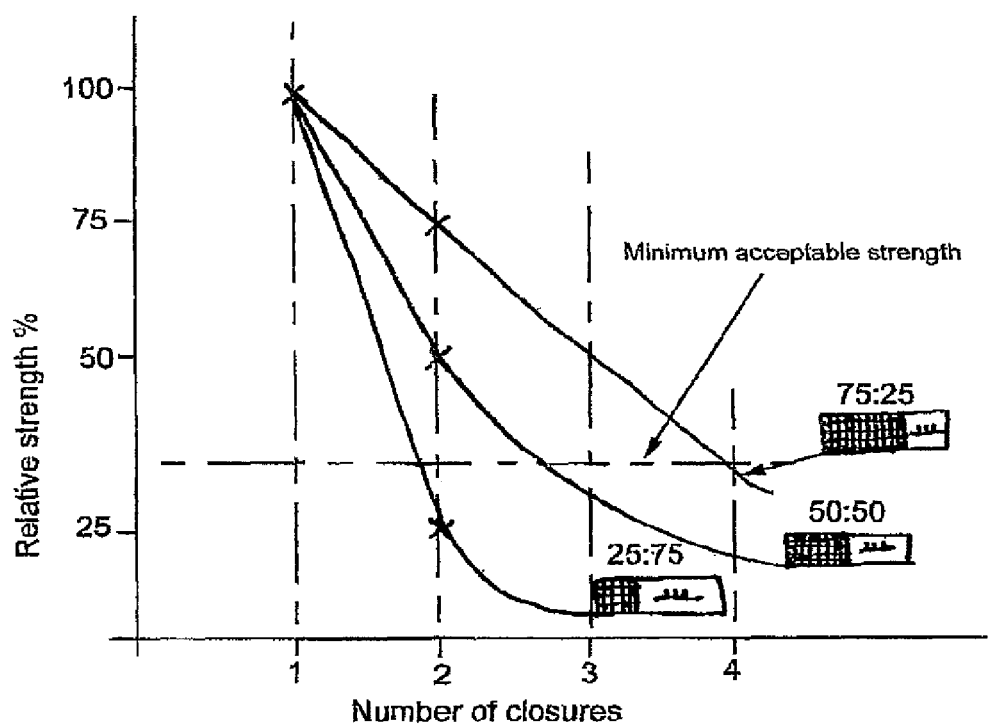

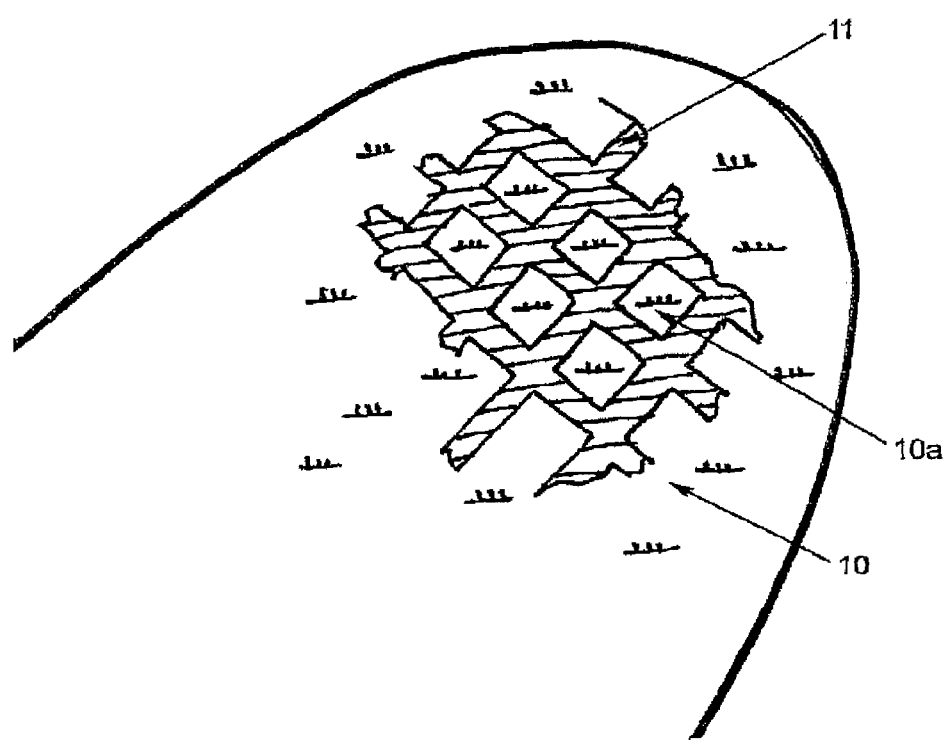

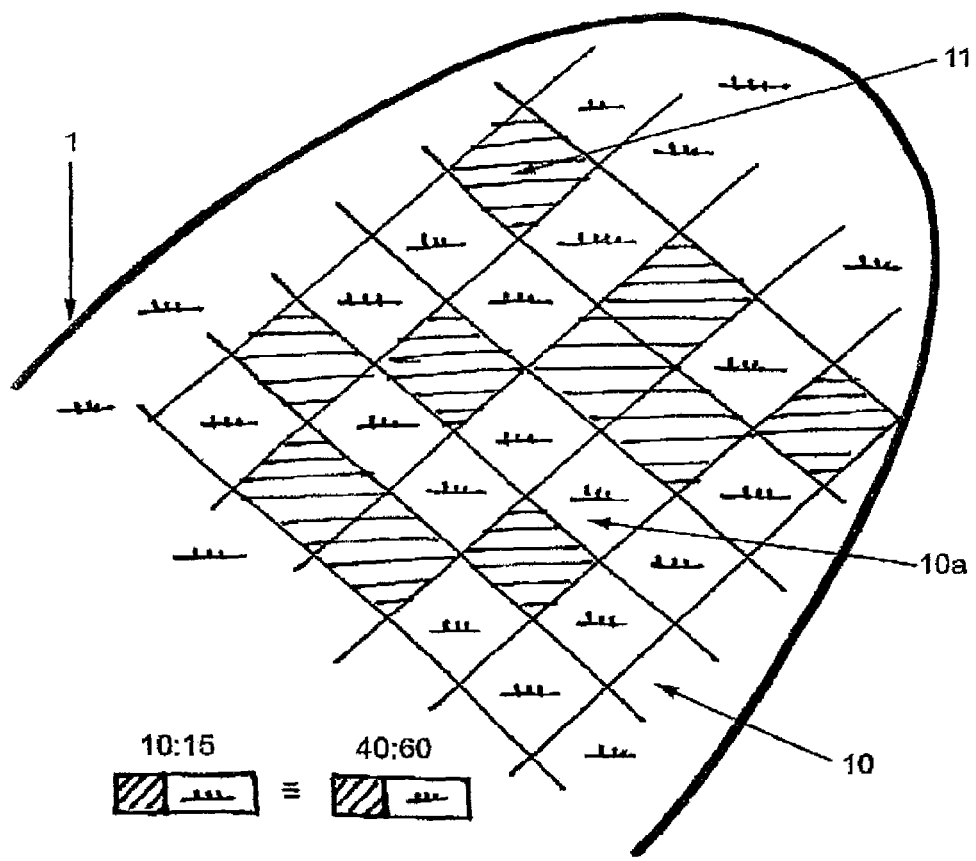

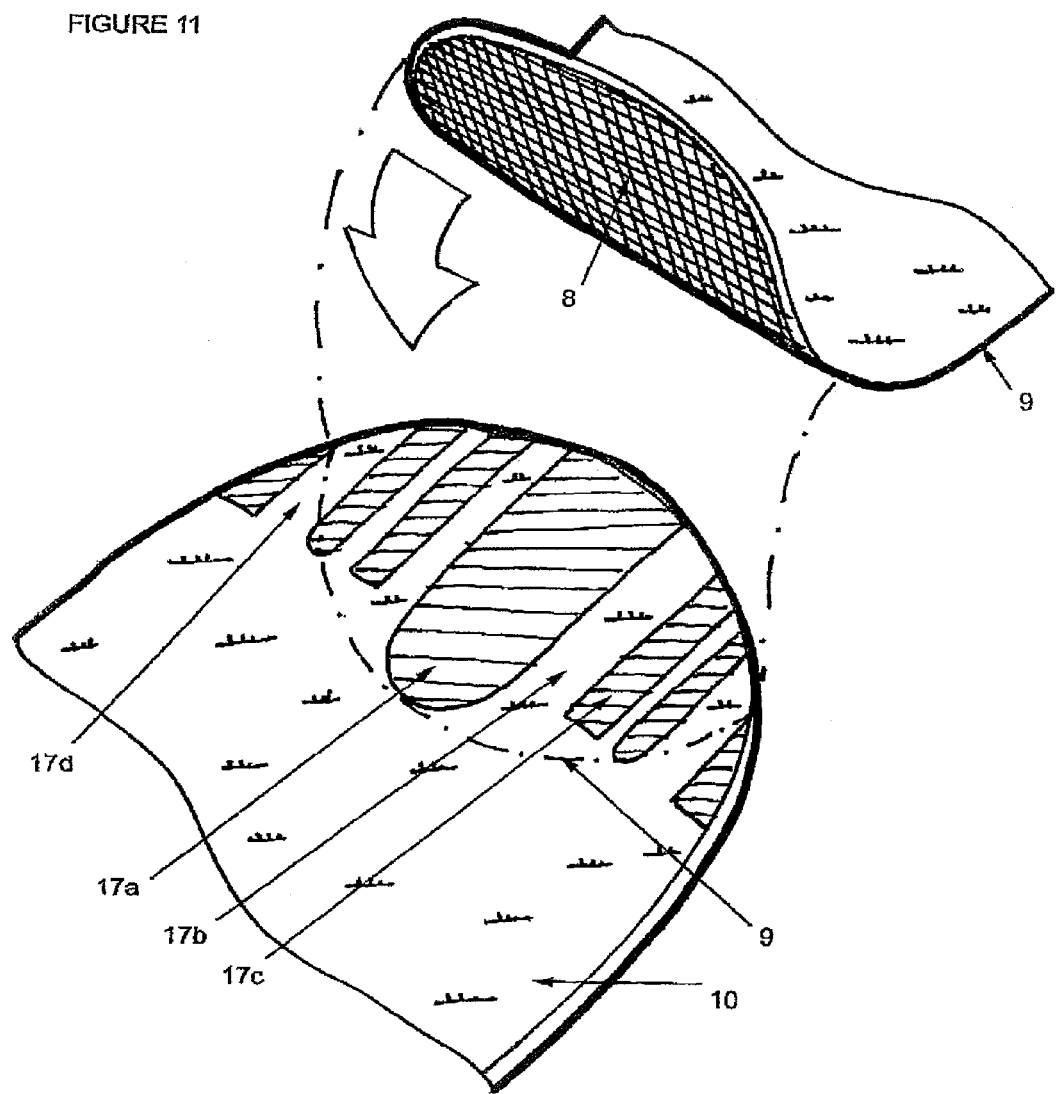

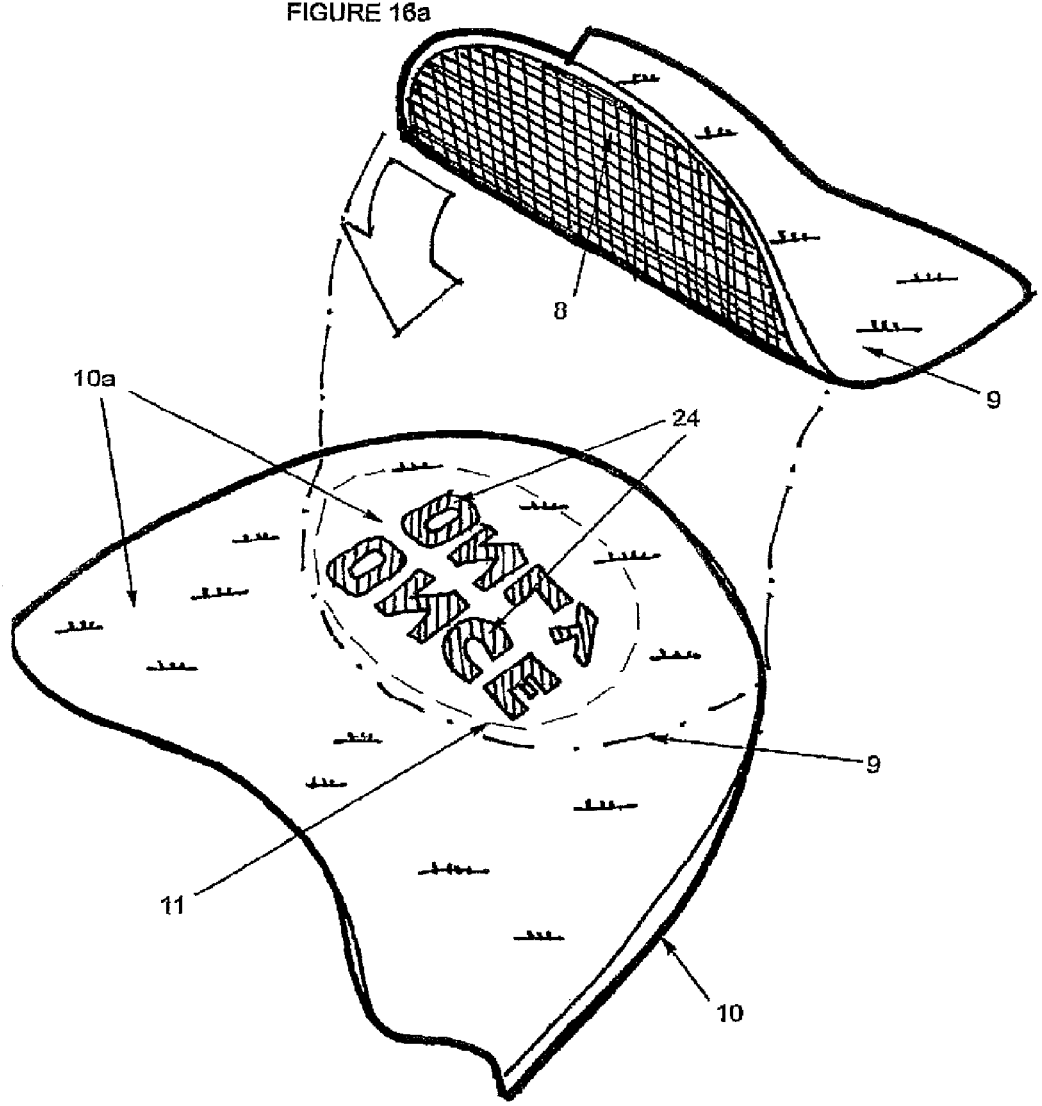

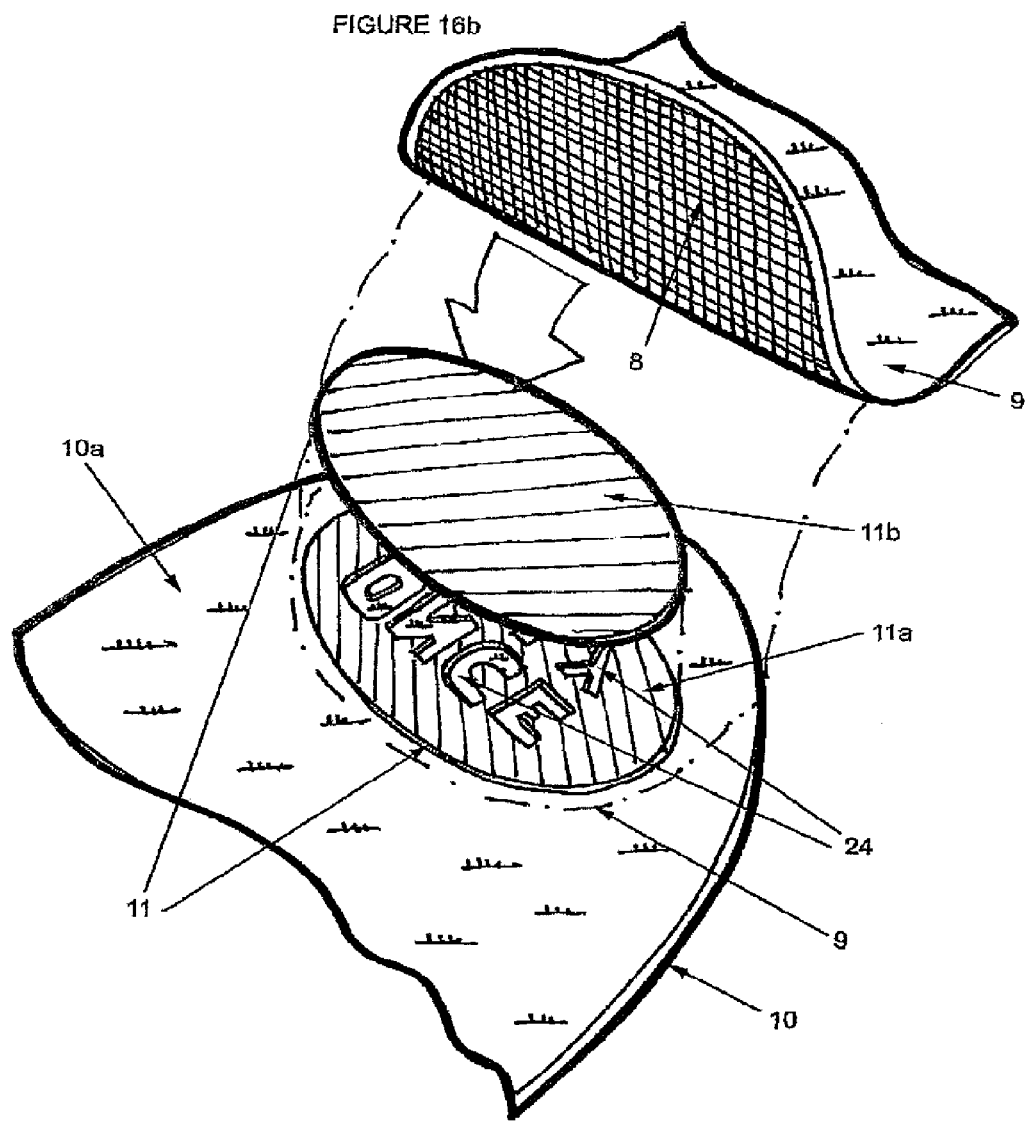

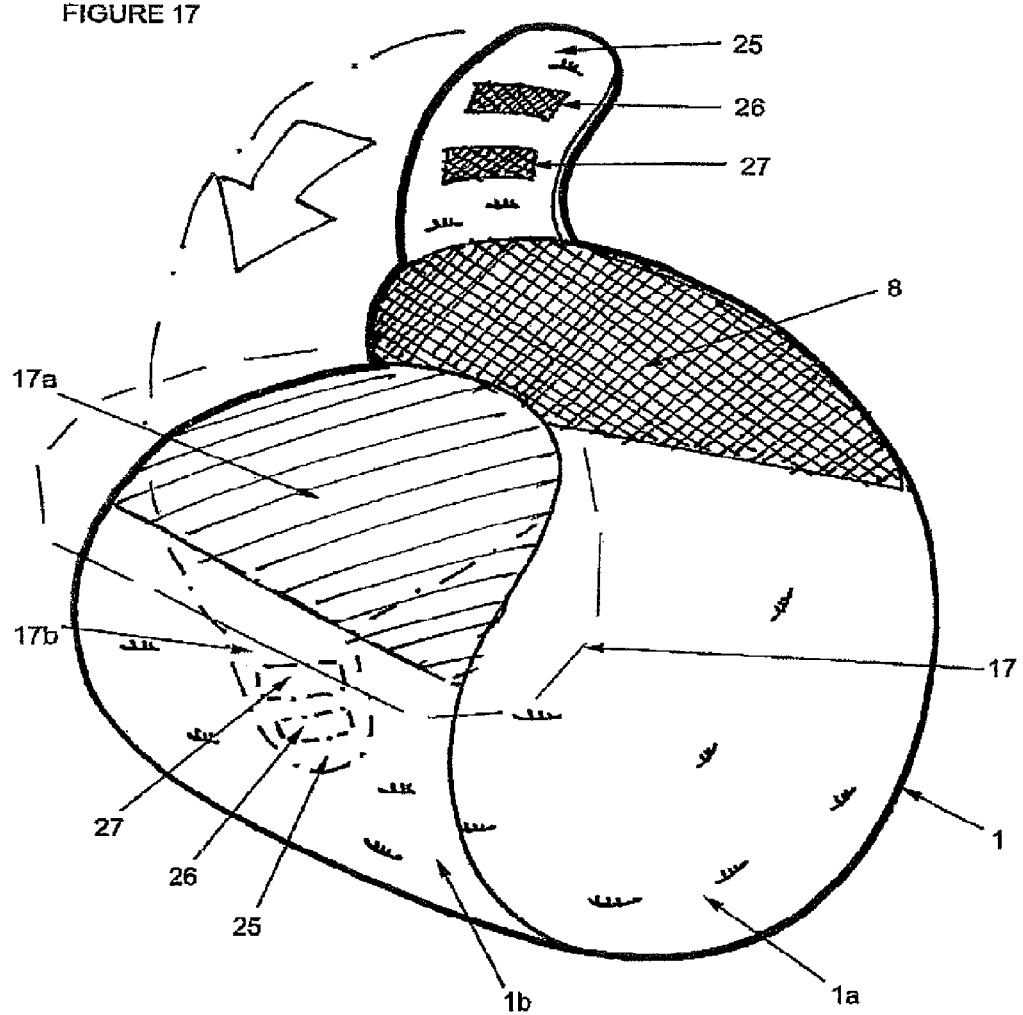

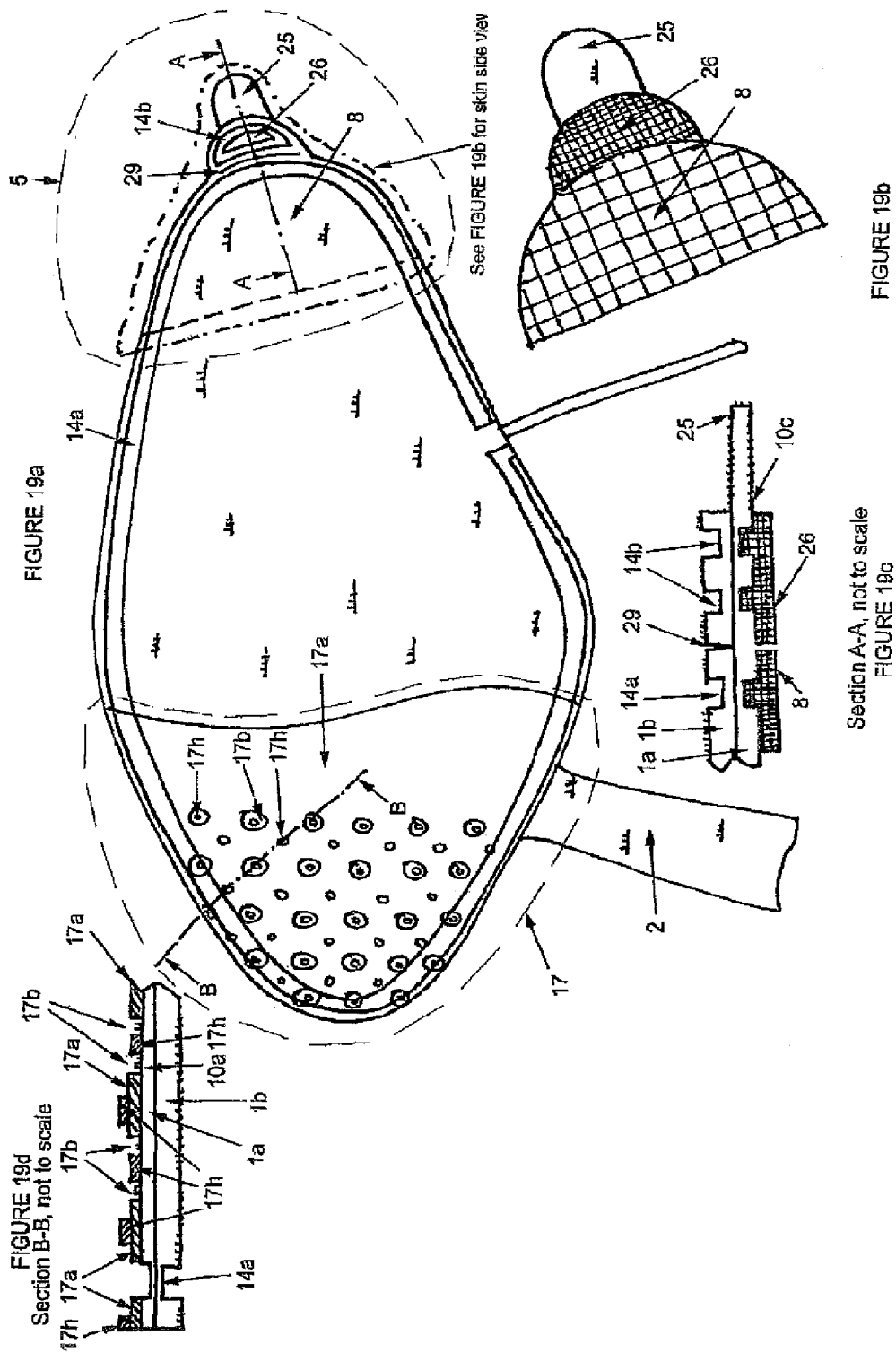

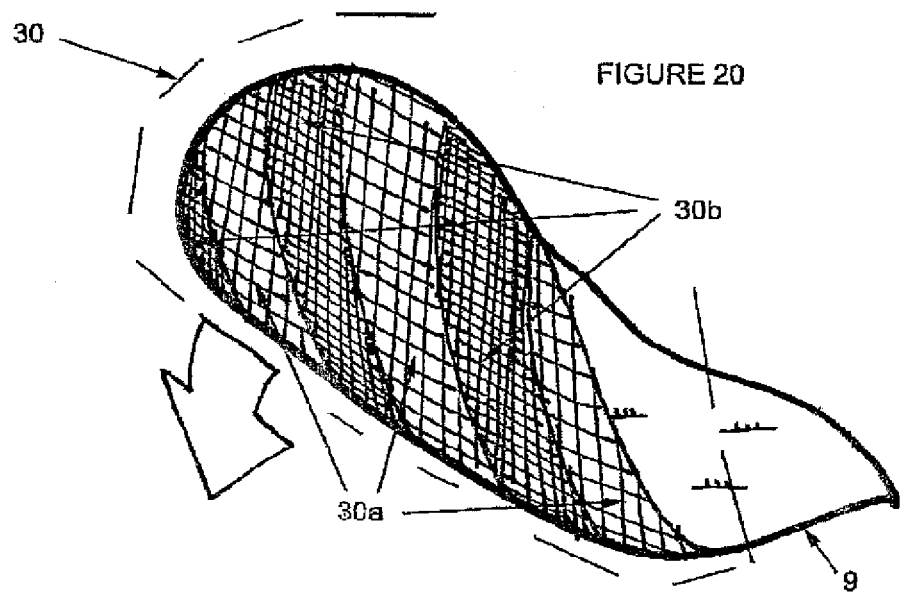
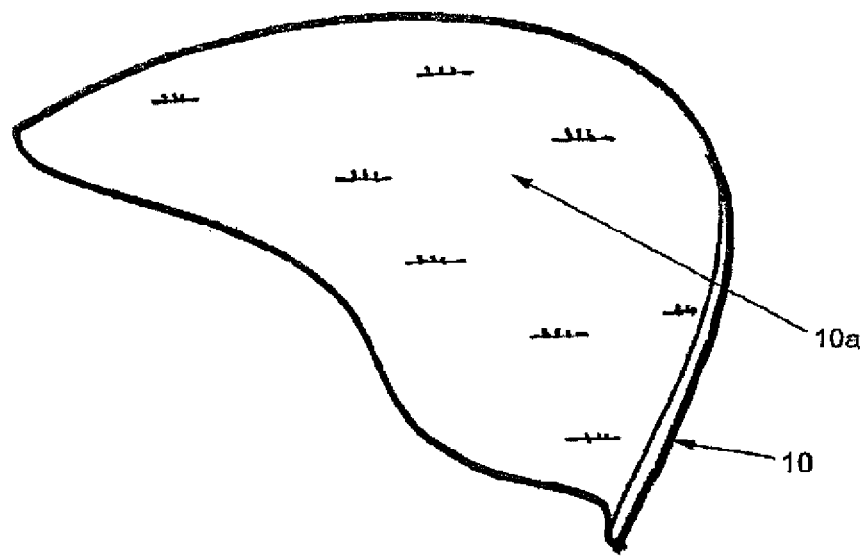
FIGURE 20

LIMITED DURABILITY FASTENING FOR A GARMENT

CROSS-REFERENCE TO RELATED APPLICATION

This application is a divisional of U.S. Ser. No. 11/996,995, filed Feb. 7, 2008, which is the National Stage of International Application No. PCT/GB2006/002674, filed Jul. 19, 2006 and published as WO2007/07012812, which claims priority from Great Britain Application No. 0515294.7, filed Jul. 26, 2005, and the entire contents of each of these applications is incorporated herein by reference.

FIELD OF THE INVENTION

The present invention relates to fastenings for garments and particularly to a short life fastening for a garment for use in the medical field.

BACKGROUND OF THE INVENTION

The use of an inflatable garment applied to a limb or other area of the human body as a means of enhancing blood circulation is a well established technique with proven clinical benefits.

The garment usually comprises an inflatable bladder contained as part of or integral to a means of attaching or securing the garment about the area to be treated. During use the bladder is filled with a fluid such as air to expand and apply force to the body, directed in such a way as to empty the veins of blood. The bladder is held pressurised for a period before releasing the fluid and then the cycle repeated. The rate of filling or venting of the bladder may vary from fractions of a second to several seconds according to the application.

The garment is attached for example to the foot normally by means of hook and loop closure over the dorsum of the foot and additionally around the heel.

SUMMARY

It is an object of the invention to provide means by which the garment can be advantageously fitted to the foot by using a closure means of limited durability as would be appropriate for example to a short life, low cost garment or to an item where re-use was to be discouraged for either clinical or commercial reasons.

The preferred embodiments of the invention disclosed herein have in mind primarily existing foot impulse technology devices such as the A-V Impulse System®. There will be applications for this limited durability closure technology beyond such use in both the medical and wider areas of application where closure of one or more components are required to be made reliably more than once, but not more than several times.

According to the invention there is provided a limited durability fastening for a garment comprising at least two garment elements to be fastened together with a predetermined closure strength, each garment element being provided with a fastening member which members engage to close the fastening, and means for controlling the degradation of the closure strength of the fastening as it is opened and closed and thus the number of permissible closures of the fastening having a predetermined closure strength.

According to another aspect of the invention there is provided a short life impulse therapy garment for the foot comprising a foot wrap and an ankle strap for retaining the foot wrap on the foot, said foot wrap incorporating an inflatable bladder for location in the plantar arch of the foot cyclically to pump the foot in accordance with a predetermined pressure and cycle time, first and second fastening members respectively for securing the ankle strap to the foot wrap to hold the foot wrap in place and the foot wrap around the foot with a predetermined closure strength sufficient to resist separation under impulse pressure, said first and second fastening members having two garment closure parts one of which is provided with an adhesive tab or adhesively treated area and the other part being formed of a material capable of degrading the adhesive of the tab or treated area upon contact therewith, and means applied to said material for controlling the degradation of the adhesive tab or adhesively treated area so as to determine the permissible number of make or break closures of said first and second fastening devices having said contact strength required to prevent said impulse pressure from opening the fastenings.

In accordance with a yet further aspect of the invention there is provided a method of providing a limited durability fastening for a garment comprising providing one fastening garment element of the garment with an adhesive tab and/or adhesively treated area, providing another fastening garment element of the garment with a contact zone or zones formed of a material capable of degrading the adhesive of the tab or treated area upon contact therewith, and modifying the garment material at said contact zone or zones to control the degradation of the adhesive tab or adhesively treated area when contact is made therebetween thereby to determine the permissible number of make and break closures of the fastening having a predetermined contact strength.

BRIEF DESCRIPTION OF THE DRAWINGS

Other features and advantages of the invention as broadly defined in the preceding paragraphs will become evident from a reading of the following description of preferred embodiments written with reference to the accompanying drawings wherein:

FIGS. 5a, 5b, 5c and 5d show cross-sectional views of various embodiments of the fastening in accordance with the invention;

FIGS. 6a and 6b show in cross-sectional view and plan view respectively a fastening in accordance with a further embodiment of the invention;

FIG. 6c is a graph depicting the relationship between closure strength and repeated fastenings of the embodiment of the invention as shown in FIGS. 6a and 6b;

FIGS. 7a and 7b show in cross-sectional view and plan view respectively a fastening in accordance with an alternative embodiment of the invention;

FIG. 8 is a graph depicting the relative strength of the closure fastening shown in FIG. 8 over a number of closure cycles;

FIG. 9 is a plan view showing a means of treating the surface of a normal non-woven material in a predetermined pattern to achieve the results of the invention in accordance with a preferred embodiment;

FIG. 10 is a plan view showing how the grid arrangement of FIG. 9 may be replaced by an irregular or even random disposition of surface modified zones in accordance with an embodiment of the invention;

FIG. 11 shows in isometric view a further embodiment of the invention wherein the surface modified zones and untreated non-woven zones may be arranged in a non-linear form;

FIGS. 16a and 16b show further means for identifying degradation of a closure fastening in accordance with the invention;

FIG. 17 shows in isometric view a further modification of the closure fastening in accordance with the invention to provide a combined dual closure system;

FIGS. 19a, 19b, 19c and 19d show respectively a plan view, a detail and two sectional views illustrating a complete closure system for a short life foot impulse technology garment incorporating the concepts of the present invention;

FIG. 20 illustrates a further variant in isometric view of a fastening for a garment in accordance with the present invention.

DETAILED DESCRIPTION

Figure 1:
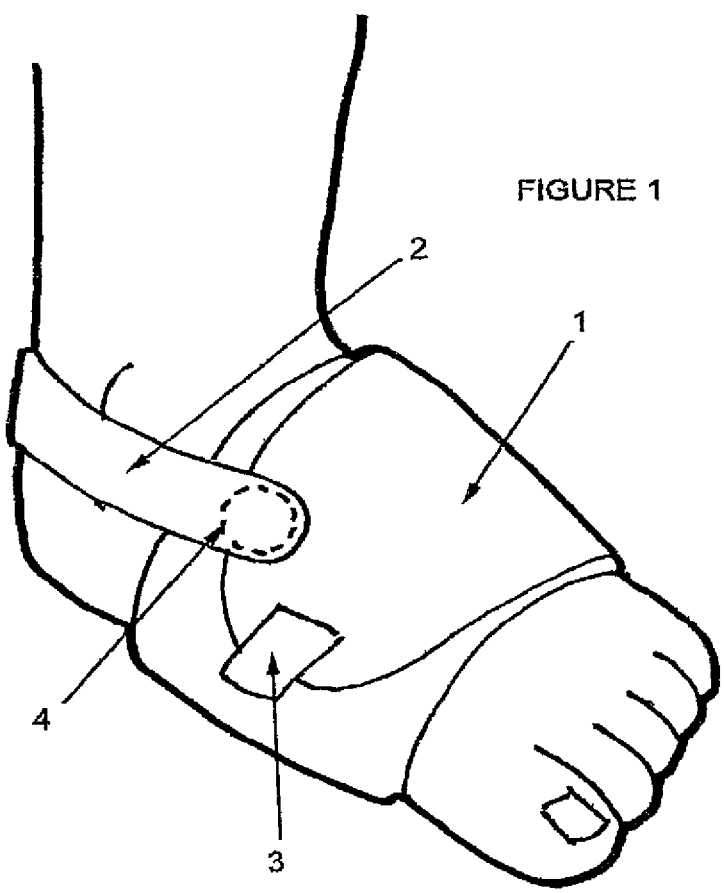
FIG. 1 is an isometric view showing a foot impulse technology garment mounted to the foot in accordance with the prior art.

The existing foot mounted impulse therapy garment shown in FIG. 1 comprises of a wrap or upper 1 incorporating a heel strap 2, both configured anatomically to conform to the foot and be secured over the foot and around the ankle. The garment is secured to the foot at the dorsum by hook closure dorsum 3 engaging with loop material being the outside facing of the upper. Similarly, the garment is prevented from sliding forward on the foot by closure of the hook closure heel strap 4 with the outer facing of the upper.

Within the garment is a bladder located between the upper and foot that is rapidly inflated in a fraction of a second to ~200 mmHg with a fluid such as air to apply force to the limb and held pressurised for up to 3 seconds before venting. The dorsum closure and heel strap closure must resist the impulsive inflation force repeatedly applied over the treatment period ranging from a few hours to several days without failure. In addition for an extended use garment the nurse or carer is required to remove the garment to inspect the condition of the patient's skin periodically before re-applying the garment. Over, for example, a 10 day period the garment may be removed and refitted 20 or 30 times and the integrity of the closure system must be maintained.

In an alternative garment intended for short application use the inclusion of a highly durable conventional hook and loop closure system need not be specified but nevertheless closure integrity must be maintained over the reduced time period and some accommodation be made to allow adjustment at the initial fit-up and singular or occasional inspection of the limb.

Figure 2:
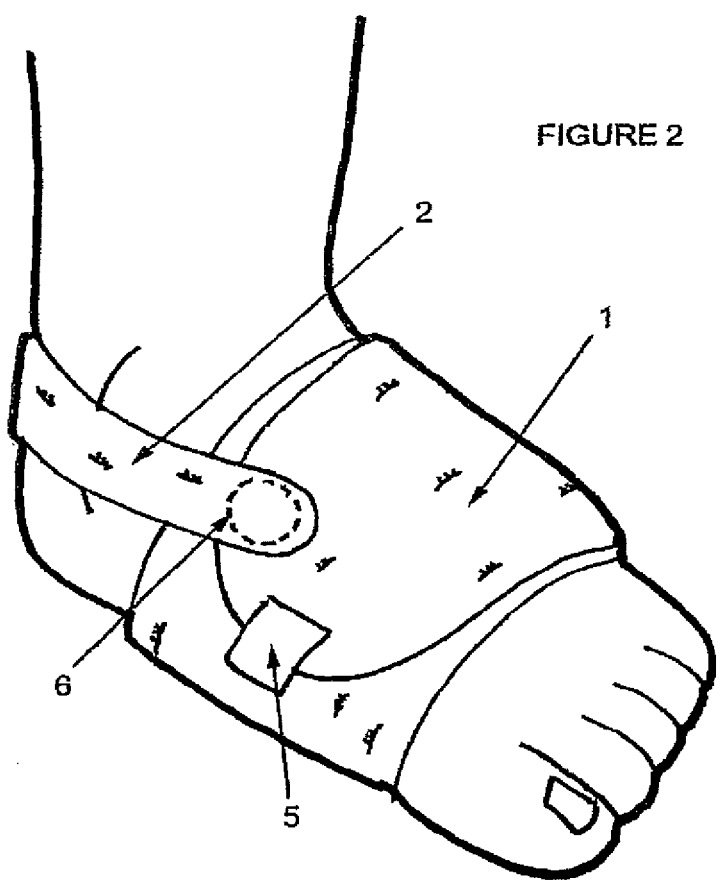
FIG. 2 is an isometric view similar to FIG. 1 but where the garment is constructed in accordance with the present invention.

FIG. 2 is an isometric view showing an alternative short life Foot Impulse Technology garment and is essentially a similar device to FIG. 1 with the alteration that the upper 1 and/or heel strap 2 are fabricated from different materials than previously. The garment is secured around the foot at the dorsum by an adhesive closure dorsum 5 engaging with the outside facing of the upper. Similarly, the garment is prevented from sliding forward on the foot by closure of the adhesive closure heel strap 6 with the outer facing of the upper.

Whereas it is conventional to utilise a fabric foam laminate material for the upper, for a short life garment a non-woven material may be specified with adequate strength, compliance and durability for the application. In the revised construction it will be recognised that the traditional mechanical closure, by engagement of the hook fastener with the loop of the fabric, has been replaced by an adhesive bond between the adhesive tab and the surface of the non-woven material.

Figure 3:
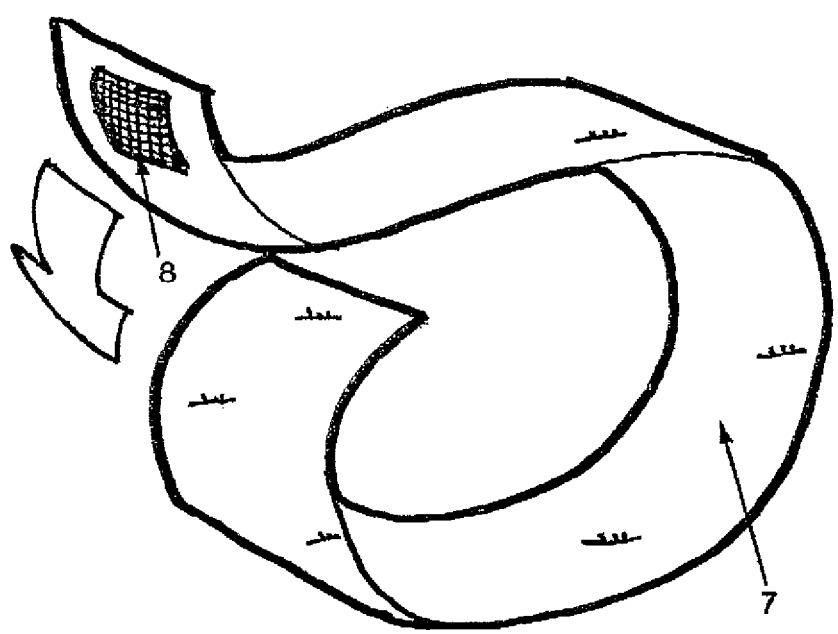
FIG. 3 is an isometric view showing a typical arrangement of an adhesive bond closure between the ends of a hoop of non-woven material in accordance with the invention.

FIG. 3 is an isometric view showing a typical arrangement of an adhesive bond closure between, for example, the ends of a hoop of non-woven material 7 using an adhesive tab 8.

A characteristic of an adhesive bond closure made between an adhesive medium and a non-woven material is that fibres of the non-woven are transferred from the non-woven to the surface of the adhesive medium when the closure is separated. According to the degree of receptivity of the adhesive and entanglement of the non-woven the transfer can range from minimal to total but the exchange may cause a degradation of the adhesion (through clogging or masking) or failure of the non-woven (through thinning or tearing) or both. Such circumstances must be carefully modified if the objective is for the closure life to exceed a single make and break closure or to avoid multiple closures. Further explanation will reveal how this may be achieved through several alternative techniques to engineer a limited durability closure system having the characteristic of adequate closure strength, for example, over 2 to 5 make and break closure cycles.

To prevent, limit or control fibre transfer from the non-woven material to the adhesive medium a means of modifying the surface or avoiding direct contact with the shedding fibres is essential.

Figure 4:
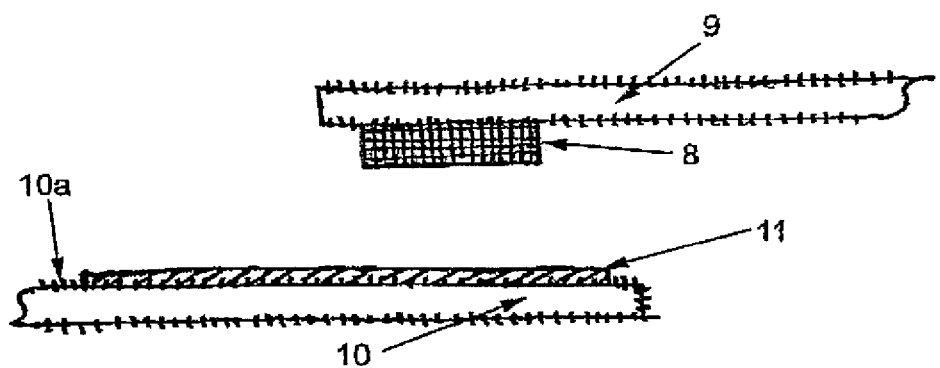
FIG. 4 is a cross-sectional view of the fastening in accordance with one embodiment of the invention.

FIGS. 4 & 5 a-d are sectional views showing alternative methods.

In FIG. 4, two non-woven components 9, 10 are to be joined by an adhesive tab 8 acting on to a surface modified zone 11 bonded to the attachment side 10a of non-woven 10. The surface modification may take the form of U.V cured ink or adhesive coating or a filmic layer applied to the engagement side of the non-woven or specifically in the more general area where the adhesive tab 8 would be attached. The purpose of the surface modified zone 11 is to bind partially free fibres along their unconnected length to the general bulk of the non-woven material and also coat the outward surface of exposed fibres to present a more homogeneous surface to mate with the adhesive tab.

Figure 5A:
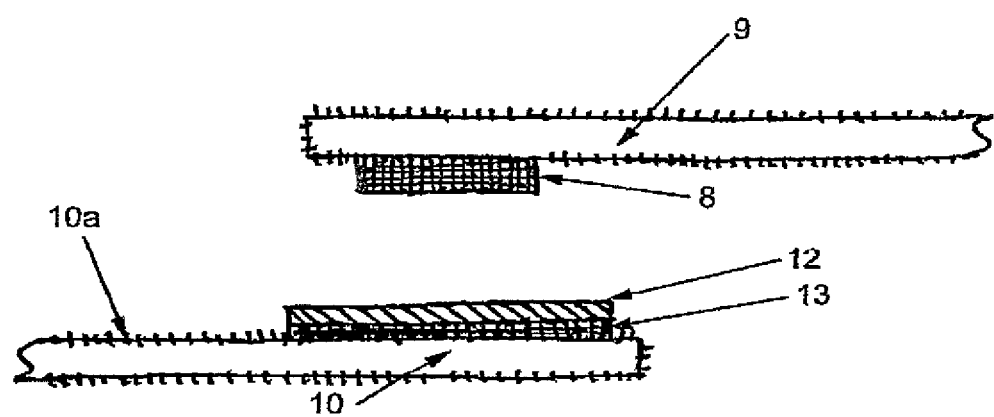

In FIG. 5a an alternative method is described whereby a separate film material applied to the non-woven material replaces the surface coating. The non-woven components 9, 10 are to be joined by the adhesive tab 8 acting on the filmic layer 12 made of a material such as regenerated cellulose, polypropylene, PVC or polyester bonded to the attachment side 10a of non-woven 10 by such means as an adhesive layer 13.

Figure 5B:
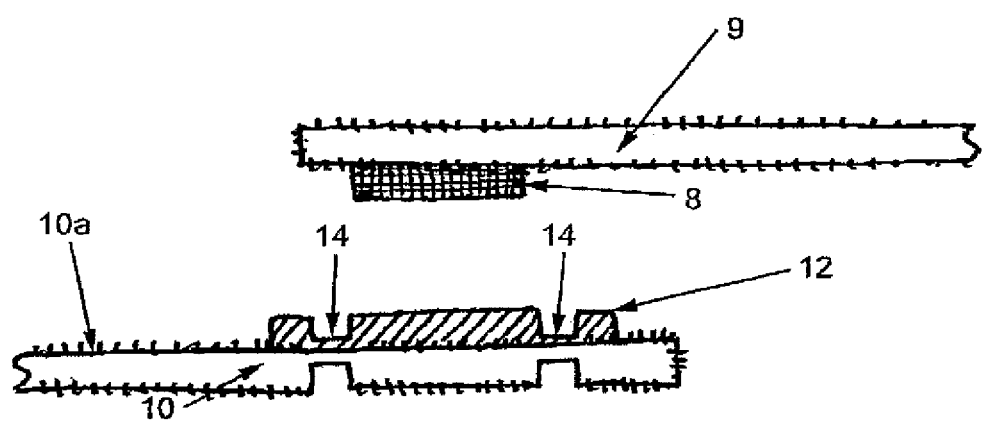

In FIG. 5b the non-woven components 9, 10 are to be joined by the adhesive tab 8 acting on the filmic zone 12 welded to the attachment side 10a of non-woven 10 by such means for example as Radio Frequency, Ultrasonic or Thermal Impulse welding with, for example, weld detail 14.

In FIG. 5c the configuration and construction is further modified to attach the filmic zone to the reverse side 10b of non-woven 10 and for film or film impregnated non-woven to be accessible on the attachment side. In the simplest of variants a series of apertures, such as illustrated by perforations 15 cut through the non-woven 10, can be arranged to partially reveal the filmic material to the adhesive tab.

Figure 5D:
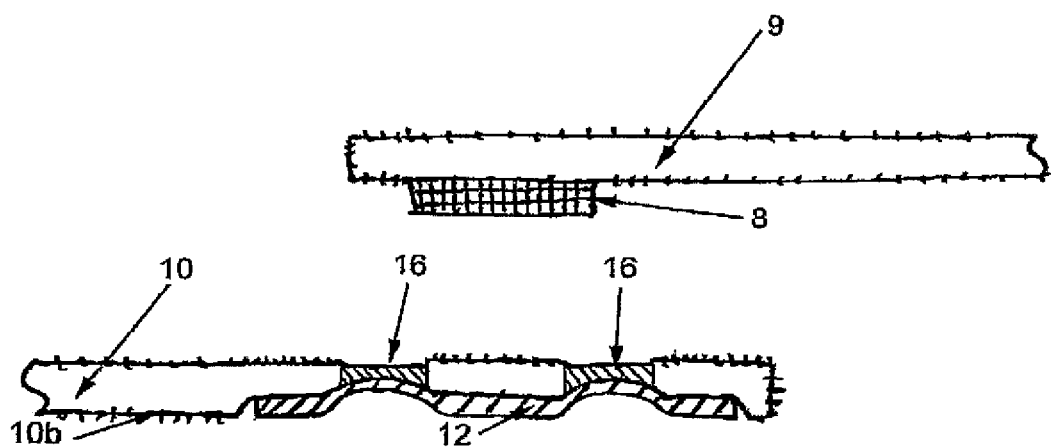

A further variant shown in FIG. 5d would provide a filmic zone by virtue of forcing filmic layer material 12 through the non-woven 10 from the reverse to the adhesive tab attachment side in a predetermined melt modified zone 16 whilst in a molten state during a welding technique such as mentioned previously.

The foregoing has described how to prepare the surface of the non-woven to be tolerant to more than a single application of an adhesive medium. In addition it is possible to engineer failure of the closure mechanism by manipulating either the quality of the surface modification or the ratio of surfaces with differing shedding characteristics, either in 2 dimensional or 3 dimensional domains.

FIGS. 6 a-c are sectional views showing the initial concept.

In FIGS. 6 a & b, two non-woven components 9, 10 are to be joined by an adhesive tab 8 acting on to a receptive zone 17 on the attachment side 10a of non-woven 10. For descriptive purposes only, the receptive zone 17 is shown as being the same area as the adhesive tab 8.

In FIG. 6c the relationship between closure strength and number of repeated fastenings is graphed. It will be realised that with each closure there is migration of the non-woven fibres from the non-woven to the adhesive tab such that the efficacy of the adhesive bond diminishes as the adhesive media becomes contaminated by shed material. Within several fastening cycles the adhesive bond will degrade below an acceptable minimum level, for example, such as is necessary to resist the impulsive inflation of a Foot Impulse Technology garment.

Figure 7A:
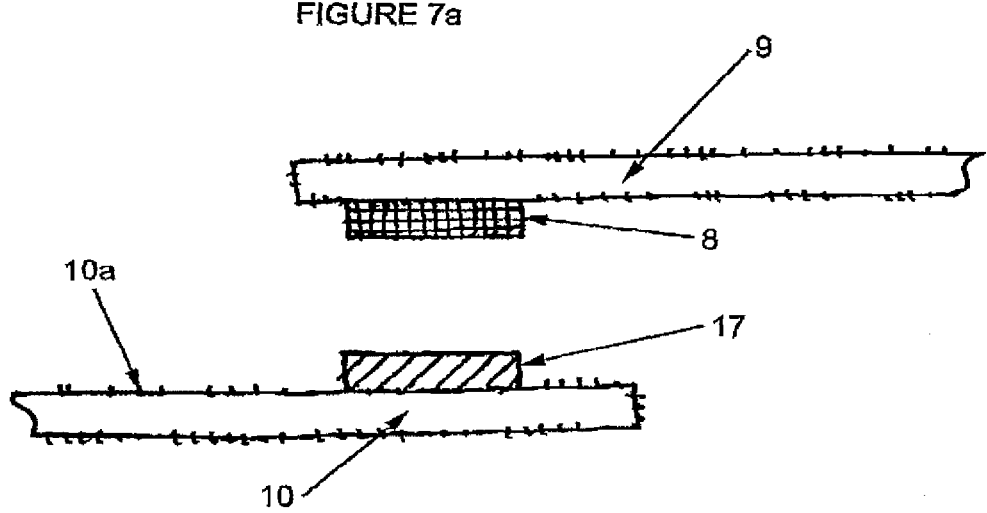

In the sectional view FIG. 7a similar to FIG. 6 and plan view FIG. 7 b, two non-woven components 9, 10 are to be joined by an adhesive tab 8 acting on to a receptive zone 17 on the attachment side 10a of non-woven 10. The receptive zone 17 comprises a surface modified zone 17a and an untreated or normal non-woven surface 17b. For descriptive purposes it should be considered that the area of the surface modified zone 17a is half that of the adhesive tab 8 and that the area of 17a plus 17b are equal to that of 8. In fact 17b is identically the same as the larger surrounding area 10 so in fact need not be specifically defined. Again, for simplification in explaining the process it should be considered that the surface modified zone 17a is essentially non destructive to the tape whereas by comparison the untreated areas 17b or 10 are wholly destructive after separation of a single union.

When the adhesive tab 8 is bonded for the first time, half of the tab area is mated with the surface modified zone 17a and half with the untreated non-woven 17b. In this ideal scenario it is assumed that perfect superimposition is achieved and that the bond strength between the adhesive tape and surface modified area and untreated area are identical although in practice this may not be exactly so. When the closure is opened for the first time half of the adhesive tab separates without deterioration from the surface modified zone whilst the other half separates and is totally destroyed by fibre take up. Should the adhesive tab subsequently be adhered in precisely the same way as the first fit the strength of the bond will be diminished and cannot be greater than 50% of the original value. In practice this ideal will not be attained as perfect superimposition is unlikely and there will be some residual strength in the sacrificial bond between adhesive tab 8 and non-woven 17b and some reduction in strength between the indestructible bond of adhesive tab 8 to surface modified zone 17a. Nevertheless, the closure strength may be engineered and manipulated to deteriorate over a few closure cycles in a controlled manner.

It is clear that other ratios of surface modified zone to untreated non-woven are equally possible and the ratio can be tailored to enhance or diminish the limited durable life of the closure system.

FIG. 8 is a graph showing the effect that variation in the surface modified zone to untreated non-woven ratio has on relative strength over a number of closure cycles. A minimum acceptable strength is also indicated such as, say 35% of maximum strength. Taking the ratio of surface modified zone to untreated non-woven zone as 50:50, the initial strength is 100% after the first closure and 50% after the second for reasons explained previously. Clearly this ratio will continue to allow the closure to function as the relative strength after the second closure exceeds the minimum acceptable strength. However, in comparison if the surface modified zone to untreated non-woven ratio is 25:75 the relative strength is less than the minimum acceptable strength threshold after the second closure and failure will occur in the closure when the Foot Impulse Technology garment is impulsed. For the examples of ratio 50:50 and 75:25 there will be a practical deterioration as explained previously leading to anticipated failure after the third and fourth closures as suggested.

FIG. 9 is a plan view showing that in practice more than a single cell of surface modified zone and untreated or normal non-woven may be utilised. Item 11 is the surface modified zone and 10a the attachment side of the unmodified non-woven 10 of for example the upper 1 being part of the construction of a Foot Impulse Technology garment as referred to earlier. Clearly the ratio and proportions of items 11:10a may be described to provide a linear grid of variable adhesion and ablation on the surface of the garment upon which an adhesive closure tab may be mated.

FIG. 10 is a plan view showing that the grid may be replaced for example by an irregular, or even random, disposition of surface modified zones 11 where the influence of repetition may be significant or non-significant in comparison with the untreated non-woven areas 10a as part of the whole 10 and in comparison with the area of the adhesive closure tab. Whilst the example depicts rectangular and repeatably sized areas 11 and 10a these may also be of other regular forms such as for example squares, circles and hexagons either of singular or multiple sizes or irregular free form shapes of singular or multiple sizes.

FIG. 11 is an isometric view further showing that the surface modified zones and untreated non-woven may be arranged in a non-linear form where the dimensions and relative proportions of each are configured for additional benefit. Surface modified element 17a is significantly larger area than surrounding lands, for example non-woven zone 17b and the next adjacent surface modified element (small) 17c such that preferential adhesion will occur, in this particular example, in the central portion of upper non-woven fabric 10 when closure is made with non-woven 9 incorporating adhesive tab 8. In addition ablation of the adhesive tab may be maximised in areas of relatively large untreated non-woven coverage (large) as shown for example at 17*d*. One practical benefit of asymmetrical or non-linear apportionment of the adhesive tab closure area is to provide maximum strength to resist the shear force imposed on the closure means by impulsing of a Foot Impulse Technology garment whilst permitting easy peel of the overlying component from the edges should removal be desired.

FIG. 12 is a sectional view illustrating the possibility of adapting the surface modified area to provide differential ablation capability. It is assumed in this eventuality that the surface modified area is of regular size, shape and disposition for simplicity but this is not mandatory.

The non-woven component 10 is processed on the attachment side 10*a* to provide surface modified elements such as 17*e*, 17*f* and 17*g* where the process is selected either to apply a pre-determined weight or thickness of media onto the non-woven or a fixed allocation of media applied at different pressure to compress the surface fibrous element on the attachment side 10*a*. Three examples are shown; at 17*e* the effect is merely to coat or bind the protruding surface fibres a minimal amount shown as 1% (or 99% unbound) to achieve an extremely weakly re-enforced non-woven, at 17*f* the coating is thicker, either fully encapsulating virtually all the surface fibres or fully compressing the fibres and coating the surface to achieve 99% bound (or 1% free), whilst 17*g* illustrates the mid point equating to 50% binding. Clearly when an adhesive tab is applied as discussed previously the robust surface modified element of 17*f* will permit more make and break closures than the weakly bound surface of 17*e*, or conversely the area of 17*e* will have a more limiting effect on the durability of the closure than would 17*f*, whilst a formulation offering the mid range option 17*g* may provide the desirable life compromise of say, more than 1 but less than 5 closure and open cycles.

Figure 12A:
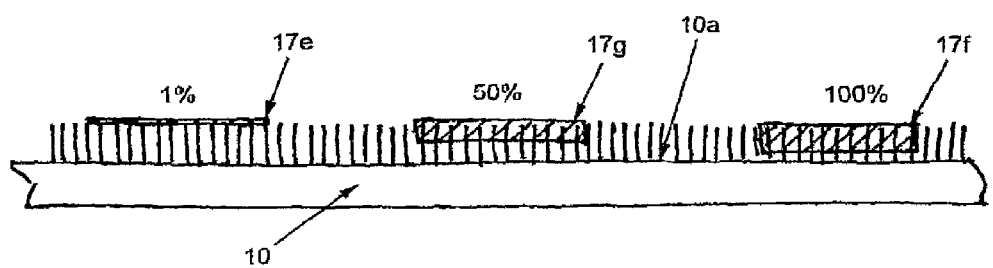
FIGS. 12a and 12b illustrate in sectional view a further possibility of treating the surface of unwoven material to provide a variation of ablation capability.
Figure 12B:
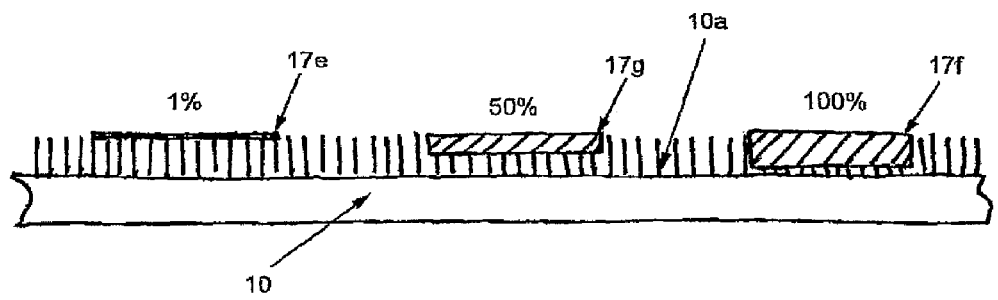

In both examples FIGS. 12*a* and 12*b* the process may be selected either to apply a pre-determined and constant weight or thickness of media such as at 17*e* and 17*f* whereby the method of process application e.g. printing pressure and/or media viscosity would modify the rate of absorption of media by the non-woven component 10. Such a method would permit, for example, design options ranging from a weakly bonded, readily detachable surface modified zone of significant and reliable thickness to a homologous, permanent and irremovable zone entangled with the non-woven component.

Furthermore, such ideas as explained in FIG. 11 could be considered to constitute a 3 dimensional element to the closure mechanism which may or may not be combined with the 2 dimensional arrangements disclosed in FIGS. 7-11.

Figure 13A:
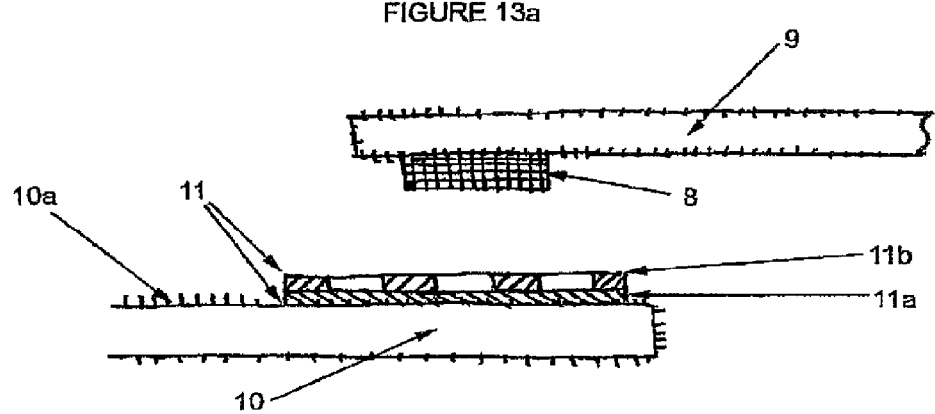
FIGS. 13a and 13b shown in cross-sectional and exploded isometric view a means of obtaining a variable thickness bonding coat to form the surface treated zone in accordance with an embodiment of the invention.
Figure 13B:
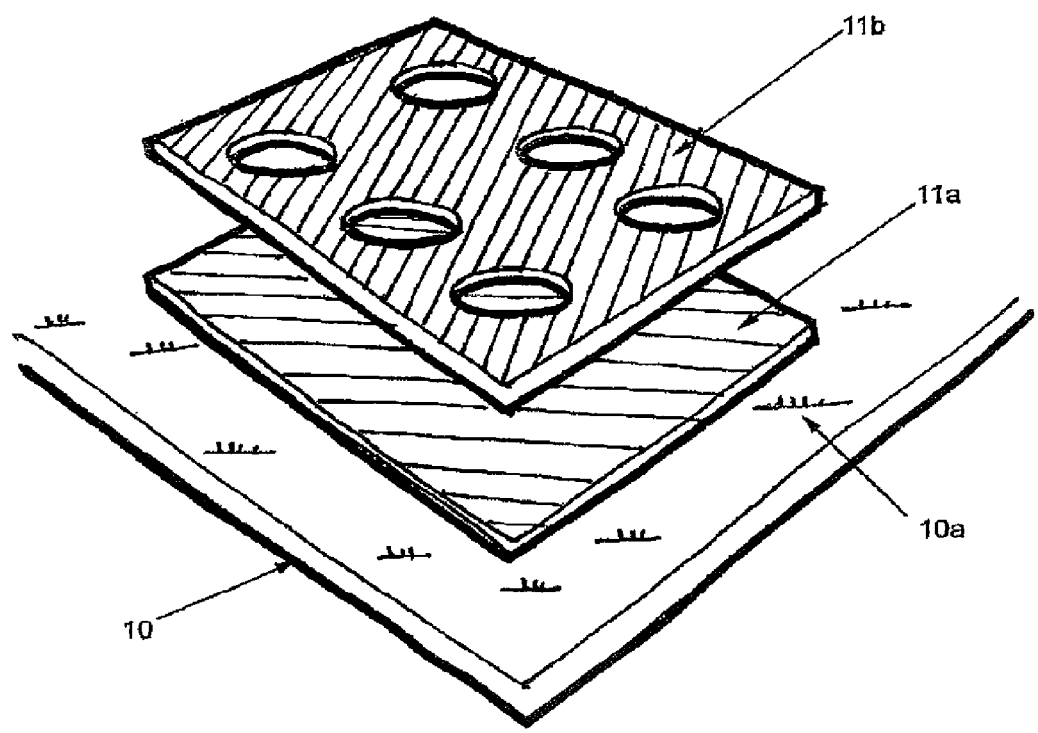

FIG. 13*a* is a sectional view and FIG. 13*b* an exploded isometric view showing a means of obtaining a variable thickness bonding coat form of surface treated zone as previously described in FIG. 4 by printing or applying an ink, varnish, adhesive or similar medium more than once.

Two non-woven components 9, 10 to be joined by an adhesive tab 8 acting on to a surface modified zone 11 on the attachment side 10*a* of non-woven 10. The surface modification may take the form of ink or adhesive coating applied to the attachment side of the non-woven or specifically in the more general area where the adhesive tab 8 would be attached. Item 11*a*, the surface modified zone layer 1 medium is applied directly to the attachment side 10*a* and is applied consistently over the entire area, followed by item 11*b*, the surface modified zone layer 2 applied in selective areas only, for example as illustrated by perforated holes to produce a general overall covering of variable but controlled thickness, weight or compaction of the surface fibres. As previously this method of 3 dimensional coating is not bounded by any limitation as to the permutations of shape, size or coverage, which in general may be engineered, between zero and total for maximum benefit.

Furthermore, the same method can be employed with the first layer 11*a* may be a continuous filmic layer and the second layer 11*b* a perforated filmic layer. In both examples the layers 11*a* and 11*b* may be transposed.

Figure 14:
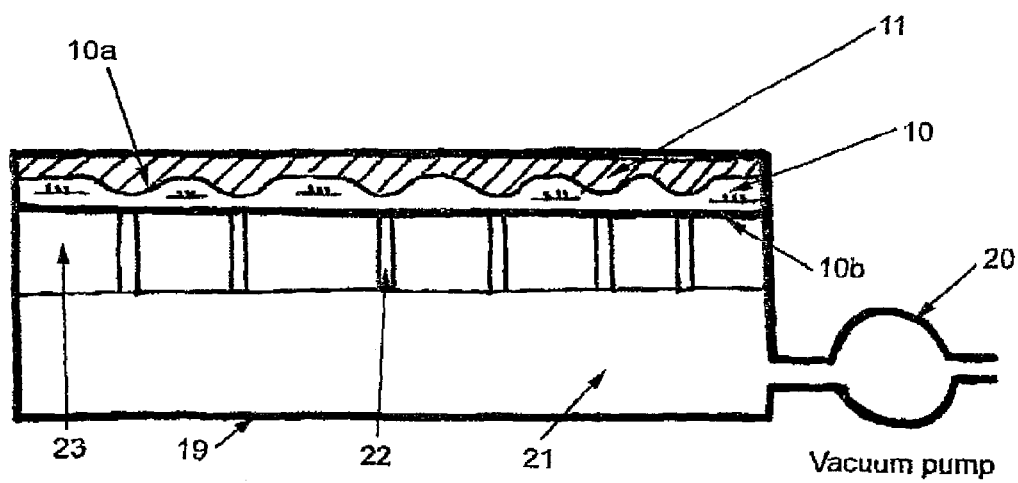
FIG. 14 shows a sectional view of a means of applying a bonding coat to the surface of a non-woven material to provide the fastening device in accordance with the invention.

FIG. 14 shows a sectional view of non-woven materials 10 with a bonding coat provided by a surface modified zone 11 applied to achieve variable penetration of the coating into the non-woven. The surface modified zone is applied to the non-woven material in conjunction with vacuum apparatus 19. A vacuum pump 20 produces a negative pressure in chamber 21, which in turn is applied through a series of appropriately sized and spaced holes 22 to the atmospheric surface side of the vacuum bed 23. When a media of low viscosity is applied to the attachment side 10*a* of the non-woven component 10 and a negative pressure selectively applied to the reverse side 10*b* of a porous material such as a non-woven, the media is drawn into the non-woven in a locally preferential or generally 3 dimensional manner. Clearly, and as explained previously the adhesion and ablation characteristics will be modified in sympathy with the absorption of media into the non-woven.

Figure 15:
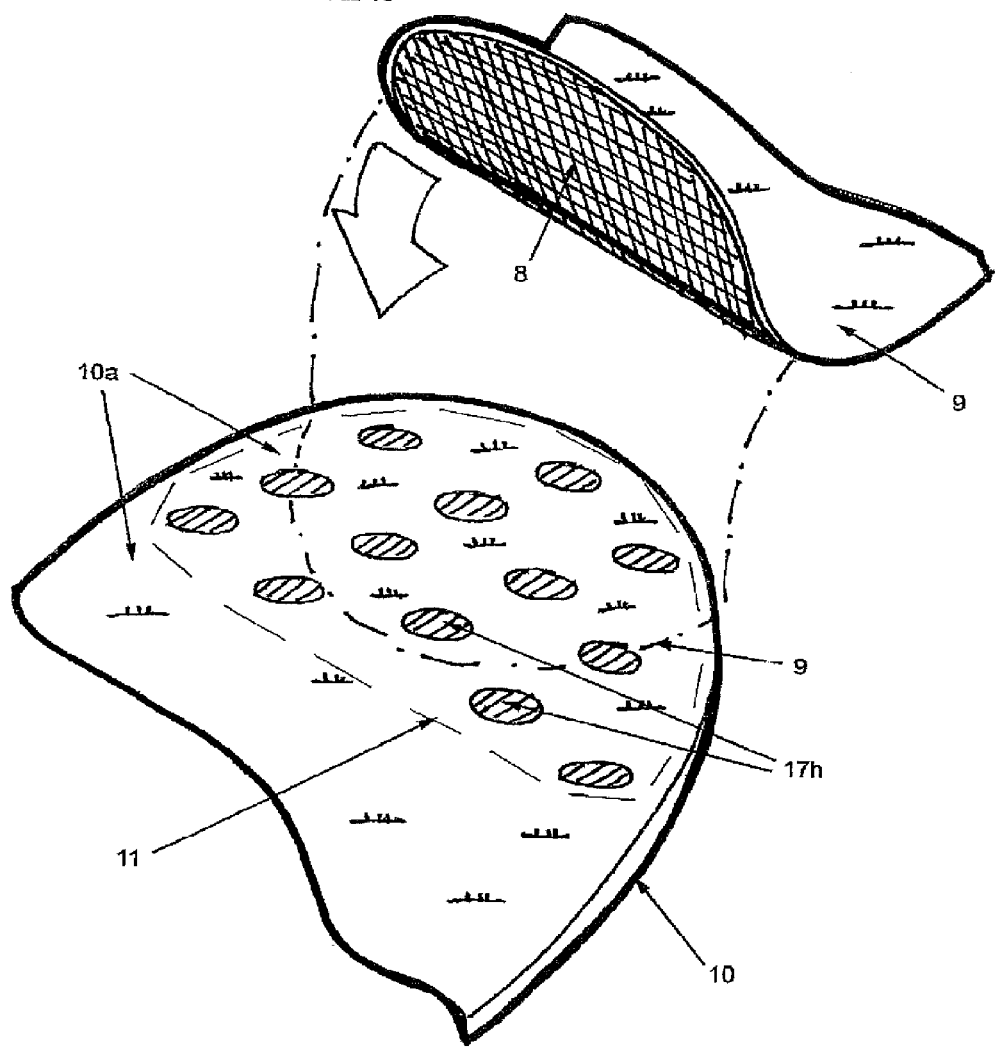
FIG. 15 is an isometric view illustrating a means of identifying degradation of the closure fastening in accordance with the invention.

FIG. 15 is an isometric view illustrating a useful effect that may be used to demonstrate contamination of the adhesive tab to the operator or nurse through repeat closure applications.

It shows an isometric view of two non-woven components 9, 10 to be joined by an adhesive tab 8 acting on to a surface modified zone 11 bonded to the attachment side 10*a* of non-woven 10. The surface modification may take the form of ink or adhesive coating applied to the attachment side of the non-woven or specifically in the more general area where the adhesive tab 8 would be attached.

In this variant the general surface modified zone 11 is applied, for example as a series of circular dots, surface modified element (dots) 17*h* that to a degree have an affinity for the adhesive tab 8. Each time a closure is made and then opened between the adhesive tab and surface modified zone an amount of shedding of surface modified element (dots) and surrounding non-woven occurs and is transferred from the untreated non-woven surface 10*a* and/or surface treated elements 17*h* to the adhesive tab 8. The surface modified elements (dots) are preferably coloured to contrast with the appearance of the adhesive tab such that whilst the shedding of non-woven onto the adhesive tab may be distinguished by those knowledgeable in the process, the contamination of the adhesive tab by a contrasting colour may be clearly appreciated by all and the level of coloured contamination used to signify the amount of closure degradation.

FIG. 16*a* is an isometric view showing a further embellishment when the transfer of media is used to convey a message to the operator or nurse.

It shows an isometric view of two non-woven components 9, 10 to be joined by an adhesive tab 8 acting on to a surface modified zone 11 bonded to the attachment side 10*a* of non-woven 10.

In this variant the surface modified zone 11 is applied, for example as a legend, symbol or icon 24 that to a degree has an affinity for the adhesive tab 8. When closure is made and then opened between the adhesive tab and surface modified zone an amount of shedding of surface modified zone and surrounding non-woven occurs and the legend, icon or symbol is transferred from the attachment side 10*a* of non-woven surface 10 and/or surface treated zone 11 including descriptive legend 24 to the adhesive tab 8. The descriptive legend is preferably coloured to contrast with the appearance of the adhesive tab such that the information is transferred and clearly legible on the adhesive tab. As a means of disguising a message it may be written as a mirror image and/or obscured as the embedded and weakly bonded text, as alluded to previously, by amalgamation into a general area of coverage provided by a 2 layer surface modified zone.

An alternative approach shown in isometric view FIG. 16b would be to convey the message through removal of media from the surface modified zone, indicated as a 'reversed out' marking in natural non-woven colour surrounded by residual unlaminated contrasting media.

A surface modified zone 11 comprises of item 11a, a surface modified layer 1 containing the legend, symbol or icon 24 applied to the attachment side 10a of non-woven 10 and a further layer, item 11b a surface modified zone layer two applied on top of 11a as described previously to achieve a less durable bonding coat in the descriptive area. Alternatively the positions of 11a and 11b may be reversed. Removal of the closure will reveal the legend preferentially on the surface modified zone and/or adhesive tab.

FIG. 17 is an isometric view of the inner and outer surfaces of a short life Foot Impulse Therapy garment and comprises of a non-woven upper 1 formed from the joining of upper skinside 1a to upper outside 1b as described previously. In this variant a pull tab 25 extends from the upper skinside either included as part of the integral profile of item 1a or as an additional joined component. An adhesive tab 8 is secured to the underside of the upper skinside 1a so as to engage with the receptive zone 17 at the other end of the garment and in particular with the surface modified zone 17a when it is fitted around the foot as described previously. In addition further adhesive components are secured to the underside of the pull tab 25, shown for example as two separate but similar components identified as anchor tabs 26, 27, so as to engage with the other end of the garment at the receptive zone 17 but beyond the surface modified zone 17a, generally on to the untreated or normal non-woven element 17b.

The essential improvement in this variant is to separate the elements of the closure into two distinct closure zones thereby offering a combined dual closure system.

In the first closure zone the integrity of the garment to resist the stress of rapid inflation is accomplished by closure of the adhesive tab 8 onto the surface modified zone 17a. In this instance the bond between adhesive tab 8 and surface modified zone 17a is engineered for maximum strength coupled with the ability to repeatedly close and open several times without significant deterioration of the bond strength, that is within the intended short life of the garment a multiple use of this closure is desirable without performance being substantially compromised.

In the second closure zone the limited durability of the garment is defined by closure of either or both anchor tabs 26, 27 on to the untreated or normal non-woven element 17b. In this instance, and in complete contrast to the performance of the first closure zone, the bond between anchor tabs 26, 27 and untreated or normal non-woven element 17b is engineered for adequate strength coupled with the ability for preferably single use closure only.

On separation, the anchor tabs 26, 27 are contaminated by pick-up of fibre shed from the surface of the non-woven thus reducing the adhesive bond strength should re-closure be attempted. As shown, the possibility exists for two satisfactory closures by utilising first anchor tab 26 alone and once this has been closed and re-opened additionally anchor tab 27. Furthermore, the adhesive strength may be engineered to offer a third closure application by using both anchor tabs 26, 27 together one more time provided their combined strength is sufficient. It will be appreciated that various combination of single and multiple anchors or orders of application will provide a limited durability feature and the method need not also be limited to the two anchor tabs referred to for simplicity.

Throughout this description no mention has been made of release liners to protect the surface of the adhesive prior to adhesion as it is presumed someone skilled in the art would be knowledgeable of this requirement.

As well as providing the life limiting feature of this combined dual closure system the anchor tab(s) perform the essential role of ensuring that the hemispherical edge of the adhesive tab 8 does not begin to lift through peel as a result of inflating the garment. Provision of a pull tab remote from the hemispherical end allows the stress of inflation to be reduced by extension along the length of the pull tab, the pull tab to be attached to the untreated or normal non-woven element 17b in an area of the upper 1 that is at lower stress and expansion, than for example the area of the inflation bladder, and an anchoring or holding down effect on the hemispherical edge of the adhesive tab 8 when the garment is fitted and closed as a hoop around the foot.

Figure 18A:
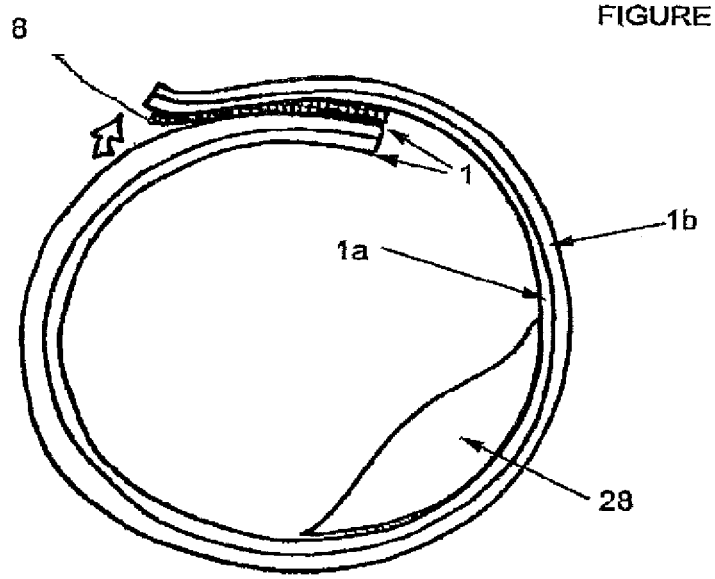
FIGS. 18a and 18b show the improved modification to the closure fastening in accordance with the invention provided by the modification illustrated in FIG. 17.

The preceding configuration with reference to FIG. 17 is illustrated with reference to FIG. 18a and FIG. 18d. FIG. 18a is a simplified cross sectional drawing where for convenience the section through a foot is considered to be circular. The upper 1, comprising a joined upper skinside 1a and upper outside 1b that may be closed as a hoop with adhesive tab 8. When a bladder 28 is inflated the hoop stress developed in the upper 1 applies a shear force between the adhesive tab 8 and its bond to the upper skinside 1a and the closure between the adhesive tab 8 and the upper outside 1b. Furthermore a differential exists between a lower hoop stress applied through the upper skinside and a higher hoop stress value applied through the upper outside causing the outermost edge of the adhesive tab to peel and curl clockwise (in the example depicted). Over time this closure will gradually open and through continued inflation and/or patient movement and interaction with bedding detach and become defective.

Figure 18B:
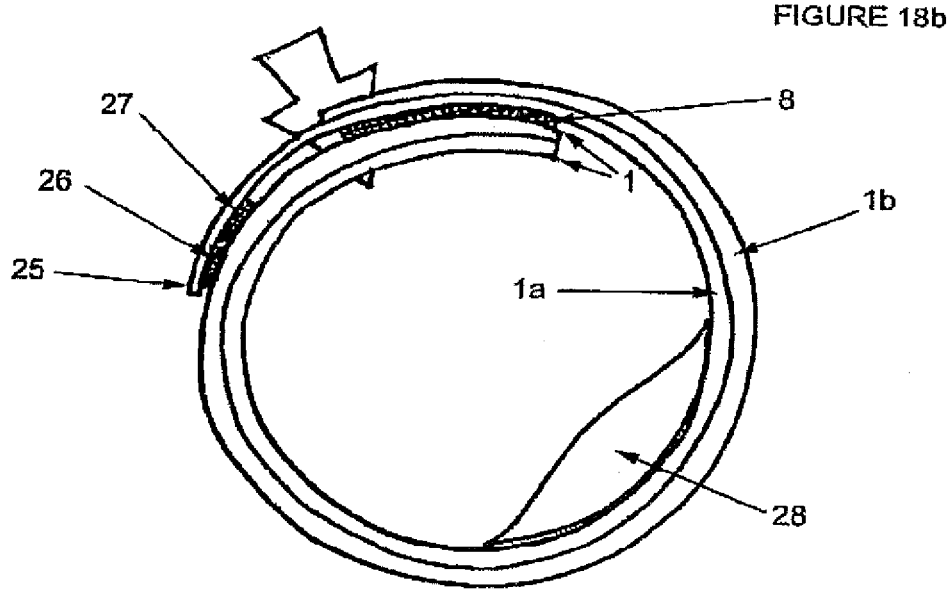

FIG. 18b is a simplified cross sectional drawing where for convenience the section through a foot is considered to be circular. The upper 1, comprising a joined upper skinside 1a and upper outside 1b closed as a hoop with adhesive tab 8 and additionally anchored by anchor tab 26 and/or anchor tab 27, on pull tab 25. When a bladder 28 is inflated the hoop stress developed in the upper 1 is applied as before but the effect of items 25, 26 and/or 27 is to provide an inward securing force holding the outmost end of adhesive tab 8 bonded to upper outside 1b to prevent the process of peel, curl, detachment and malfunction occurring.

FIG. 19a is a preferred arrangement of a complete closure system for a short life Foot Impulse Technology garment shown in plan form viewed from the outside or non-foot contact side. See also; FIG. 2 for general outline and attachment to the foot and compare those features using the same reference numerals. The right hand side of the view depicts the adhesive closure dorsum 5 and the left side the receptive zone 17 which when fitted around the foot as a hoop and secured together constitute a limited durability closure.

The upper 1, comprises an upper skinside 1a and upper outside 1b joined around the main periphery by weld detail upper 14a. Both upper components are of similar profile shape except that pull tab 25 is only included on the upper skinside.

At the adhesive closure dorsum 5 end of the garment the periphery is extended and further locally joined in the area of the anchor tab 26, by weld detail anchor tab 14b. An adhesive tab 8 of approximately hemispherical shape is adhered to the reverse side of the upper 1, specifically to the skinside of upper skinside 1*a*. In this variant the general and larger hemispherical shape is further extended from the hemispherical edge by a smaller hemispherical element. The anchor tab 26, is adhered to the extension except for the distal finger lift portion, the pull tab 25. The anchor tab 26, may be a separate component or included as part of the adhesive tab 8. The adhesive tab 8 and anchor tab 26, will be explained in more detail with reference to FIG. 19*b*.

Importantly the weld detail upper 14*a* and weld detail anchor tab 14*b* are two separate entities spaced to allow a stress relieving slit 29 to be positioned between. The stress relieving slit 29 is pierced completely through the thickness of the upper outside 1*b* over the majority of the width of the pull tab 25 leaving sufficient non-woven land attached only to prevent detachment of the pull tab element from the general upper outside, for manufacturing convenience. It should also be recognised that the stress relieving slit 29 does not penetrate the upper skinside 1*a*. The adhesive closure dorsum 5 will be explained in more detail with reference to FIG. 19*c*.

FIG. 19*d* is a cross sectional drawing showing the receptive zone 17 end of the garment with the upper skinside 1*a* joined to the upper outside 1*b* by weld detail upper 14*a* as stated previously.

The upper skinside is processed over approximately one third of the upper area as shown on the external or attachment side 10*a* by application of a surface modified element 17*a*. Surface modified element 17*a* is located so as to coincide with the position of the adhesive closure dorsum 5 when the garment is fitted to the foot as a hoop and for practical purposes is oversized compared with, for example adhesive tab 8, to accommodate a range of foot sizes and ergonomic shapes.

In detail the receptive zone 17 comprises of several features each having a different performance characteristic.

The general area is a surface modified element 17*a* which provides good receptivity with the adhesive tab 8 and anchor tab 26 and should be considered as being able to withstand multiple closure and opening cycles of the adhesive tabs without significant deterioration of the bond strength.

Within the surface modified element 17*a* are areas or zones of untreated or normal non-woven element 17*b* which by further reference to FIG. 19*a* are illustrated in this example as being of ring form, regularly spaced across the general area. As disclosed previously the form, disposition and quantity or area of untreated or normal non-woven element 17*b* is one variable used to modify performance. The function of the untreated or normal or untreated element 17*b* is to provide adhesion with the adhesive tab 8 and anchor tab 26 for the first closure and thereafter to inhibit the performance of the adhesive bond by clogging the adhesive, either preventing or reducing re-adhesion in that previously bonded region. In comparison with the general area specified for multiple closures this element is intended to be essentially single use.

The untreated or normal non-woven element 17*b*, contained by the receptive zone 17, may be further processed to provide surface treated elements (dots) 17*h* adhered to the non-woven or alternatively or additionally applied directly to the surface modified element 17*a*. These features are shown in repetitive layout FIG. 19*a* but may take other forms as described previously. The purpose of surface treated elements (dots) 17*h* is to provide adhesion with the adhesive tab 8 and anchor tab 26 for the first closure and thereafter to inhibit the performance of the adhesive bond by clogging the adhesive, either preventing or reducing re-adhesion in that previously bonded region and to reveal the fibre transfer from the non-woven component to the adhesive components in a clear way to the user. Where it is desirable to use a white coloured non-woven material in conjunction with a clear, natural, white or light coloured adhesive, deposition of the non-woven fibres on to the adhesive may be difficult to recognise by the nurse or user. If the surface treated elements (dots) 17*h* are of a contrasting colour a viable means of indicating that the limited durability closure has been closed and opened at least once is provided. Furthermore since in practical application not all of an engaged dot area would be expected to transfer on a first event and a second closure is unlikely to absolutely coincide with the original closure more contrasting material will be transferred with each opening of the closure to provide an indication of the number of closure/opening cycles completed.

Other combinations of limited durability closure can be realised with different ratios of multiple to single use areas, with or without tell tale markers on either elements.

FIG. 19*b* shows in plan view the detail of the adhesive closure element comprising the adhesive tab portion 8 and the anchor tab 26 which may be produced as one entity of particular adhesive quality or as a combination of 2 parts either of same or different adhesive quality and the non adhesive pull tab 25.

FIG. 19*c* is a cross sectional view of the adhesive closure dorsum 5 comprising the upper skinside is joined to the upper outside 1*b* by weld detail upper 14*a* and in the area of anchor tab 26, by weld detail anchor tab 14*b*. Stress relieving slit 29 is positioned between the two weld areas and is cut through the upper outside 1*b* only. The adhesive tab 8 and anchor tab 26, shown coincident in this example, are attached to the upper skinside 1*a* on the skin side 10*c*. The pull tab 25 extends from the anchor tab area to provide an accessible finger lift portion which may be gripped to separate the limited durability closure prior to removal of the garment from the foot by first peeling the anchor tab 26 from the receptive zone followed by the adhesive tab.

As described previously the combination of adhesive tab, anchor tab and stress relieving slit serve to provide an inward securing force holding the outmost end of adhesive tab 8 bonded to upper outside 1*b* via receptive zone 17 to prevent the process of peel, curl, detachment and malfunction occurring during the treatment of the patient.

As a final variant, FIG. 20 shows an isometric view of a revised arrangement having two non-woven components 9, 10 to be joined by a composite adhesive tab 30 acting directly onto the attachment side 10*a* of non-woven 10. The composite adhesive tab comprises re-useable elements 30*a* and degradable elements 30*b*. Item(s) 30*a* are engineered to be selectively re-applicable to the non-woven with low take up of fibrous materials whereas item(s) 30*b* is selected for its initial strength and ability to be readily contaminated by shed fibres from the non-woven material. In this way the relative strength may be controlled to have limited durability irrespective of preparation of the non-woven surface.

The invention claimed is:

1. A method of providing a limited durability fastening for a garment comprising providing one fastening garment element of the garment with an adhesive tab and/or adhesively treated area, providing another fastening garment element of the garment with a contact zone or zones formed of a material capable of degrading the adhesive of the tab or treated area upon contact therewith, modifying the garment material at said contact zone or zones to control the degradation of the adhesive tab or adhesively treated area when contact is made therebetween thereby to determine the permissible number of make and break closures of the fastening having a predetermined contact strength, wherein an aperture or apertures are provided in said one garment fastening element as a means of relieving the stress in the limited durability fastening, and providing a non-woven material as the material capable of degrading the adhesive tab or treated area, wherein the garment material is modified by applying a bonding coat in the form of a vapour phase media.

2. A method as claimed in claim 1 wherein the application of the bonding coat in the form of the vapour phase media is applied under the influence of negative pressure to the reverse side of the non-woven material in a predetermined pattern and varying the negative pressure to determine the final thickness, weight or ingress of the bonding coat on the non-woven material.

3. A method as claimed in claim 2 further including applying an obscured or hidden textual symbolic or iconic message on one or more of said garment elements on the adhesive tab, adhesively treated area or non-woven material by transfer or removal of defining elements.

4. A method as claimed in claim 3 further including providing a visual indication of the limited number of make and break closures by contrasting contamination of the adhesive tab or adhesively treated area.

5. A method as claimed in claim 4 wherein the contrasting coloured contamination is provided by removal depletion or deposition of contrasting coloured fibrous material from the contact zone or zones.

6. A method as claimed in claim 4 wherein contrasting contamination is provided by indication of the cumulative degree of contamination of the materials in the attachment area.

7. A method as claimed in claim 1 including degrading a closure strength of the fastening at least 50% after 4 make and break closures.

8. A method as claimed in claim 1 wherein modifying the garment material comprises changing an adhesive degrading surface characteristic of the garment material in the contact zone or zones.

* * * * *